US012239450B2

(12) United States Patent
Frankel et al.

(10) Patent No.: US 12,239,450 B2
(45) Date of Patent: Mar. 4, 2025

(54) ADAPTIVE SYSTEMS AND METHODS FOR SEIZURE DETECTION AND CONFIDENCE INDICATION

(71) Applicant: Epitel, Inc., Salt Lake City, UT (US)

(72) Inventors: Mitchell A. Frankel, Salt Lake City, UT (US); Avidor Kazen, Chicago, IL (US); Tyler James Newton, Baltimore, MD (US); Zoë Vera Tosi, Oakland, CA (US)

(73) Assignee: Epitel, Inc., Salt Lake City, UT (US)

( * ) Notice: Subject to any disclaimer, the term of this patent is extended or adjusted under 35 U.S.C. 154(b) by 0 days.

(21) Appl. No.: 18/674,580

(22) Filed: May 24, 2024

(65) Prior Publication Data

US 2024/0398322 A1 Dec. 5, 2024

Related U.S. Application Data

(60) Provisional application No. 63/511,536, filed on Jun. 30, 2023, provisional application No. 63/505,678, filed on Jun. 1, 2023.

(51) Int. Cl.
*A61B 5/291* (2021.01)
*A61B 5/00* (2006.01)
(Continued)

(52) U.S. Cl.
CPC .......... *A61B 5/4094* (2013.01); *A61B 5/0006* (2013.01); *A61B 5/0024* (2013.01);
(Continued)

(58) Field of Classification Search
CPC ... A61B 5/4094; A61B 5/7264; A61B 5/7267; A61B 5/374; A61B 5/291; A61B 5/68335; A61B 5/257; A61B 5/0024; A61B 5/6814; A61B 5/7225; A61B 5/7278; A61B 5/7282; A61B 5/743
See application file for complete search history.

(56) References Cited

U.S. PATENT DOCUMENTS 6,496,724 B1 12/2002 Levendowski et al.
6,735,467 B2 5/2004 Wilson
(Continued)

FOREIGN PATENT DOCUMENTS

EP 2782499 B1 3/2021
JP 2022536552 A 8/2022
(Continued)

OTHER PUBLICATIONS

Ceribell®, Clarity™ Pro—Revolutionary AI-Enhanced Monitoring for Neurologic Acute Care Patients. Retrieved from URL: https://ceribell.com/product/claritypro/ (accessed on Aug. 13, 2024); 9 pages.
(Continued)

*Primary Examiner* — Eric F Winakur
(74) *Attorney, Agent, or Firm* — Knobbe, Martens, Olson & Bear, LLP

(57) ABSTRACT

Disclosed electroencephalogram (EEG) monitoring and detection systems and methods can detect differentiated electrographic seizure characteristics of different seizure types across a diverse group of patients. Disclosed systems and methods can utilize EEG data collected by discrete wireless EEG sensors positioned on a scalp of a patient.

20 Claims, 20 Drawing Sheets

(51) Int. Cl.
  *A61B 5/256* (2021.01)
  *A61B 5/257* (2021.01)
  *A61B 5/372* (2021.01)
  *A61B 5/374* (2021.01)

(52) U.S. Cl.
  CPC .............. *A61B 5/256* (2021.01); *A61B 5/257* (2021.01); *A61B 5/291* (2021.01); *A61B 5/372* (2021.01); *A61B 5/374* (2021.01); *A61B 5/6814* (2013.01); *A61B 5/68335* (2017.08); *A61B 5/7203* (2013.01); *A61B 5/7225* (2013.01); *A61B 5/7267* (2013.01); *A61B 5/7278* (2013.01); *A61B 5/7282* (2013.01); *A61B 5/743* (2013.01); *A61B 2560/045* (2013.01); *A61B 2560/0468* (2013.01)

(56) References Cited

U.S. PATENT DOCUMENTS

| | | | |
|---|---|---|---|
| 8,666,484 | B2 | 3/2014 | Nierenberg et al. |
| 8,849,390 | B2 | 9/2014 | Echauz et al. |
| 8,868,172 | B2 | 10/2014 | Leyde et al. |
| 10,342,451 | B2 | 7/2019 | Girouard et al. |
| 10,448,839 | B2 | 10/2019 | Shivkumar |
| 10,463,270 | B2 | 11/2019 | Leyde |
| 10,517,541 | B2 | 12/2019 | Nierenberg et al. |
| 10,736,525 | B2 | 8/2020 | Cardenas et al. |
| 10,743,809 | B1 | 8/2020 | Kamousi et al. |
| 10,929,753 | B1 | 2/2021 | Nierenberg et al. |
| 10,980,469 | B2 | 4/2021 | Girouard et al. |
| 11,160,505 | B2 | 11/2021 | Gunasekar et al. |
| 11,857,330 | B1 | 1/2024 | Frankel et al. |
| 11,969,249 | B2 | 4/2024 | Dudek et al. |
| 2003/0074033 | A1 | 4/2003 | Pless et al. |
| 2003/0195429 | A1 | 10/2003 | Wilson |
| 2004/0068199 | A1 | 4/2004 | Echauz et al. |
| 2006/0111644 | A1 | 5/2006 | Guttag et al. |
| 2009/0124923 | A1 | 4/2009 | Sackellares et al. |
| 2010/0168603 | A1 | 7/2010 | Himes et al. |
| 2011/0082381 | A1 | 4/2011 | Uthman et al. |
| 2011/0257517 | A1 | 10/2011 | Guttag et al. |
| 2012/0101401 | A1 | 4/2012 | Faul et al. |
| 2015/0134580 | A1 | 5/2015 | Wilson |
| 2015/0216436 | A1 | 8/2015 | Bosl et al. |
| 2017/0076217 | A1 | 3/2017 | Krumm et al. |
| 2018/0289310 | A1 | 10/2018 | Girouard et al. |
| 2019/0126033 | A1 | 5/2019 | Pradeep |
| 2019/0380583 | A1 | 12/2019 | Danneels et al. |
| 2020/0022603 | A1 | 1/2020 | Cardenas et al. |
| 2021/0052209 | A1 | 2/2021 | Hecox |
| 2021/0169417 | A1 | 6/2021 | Burton |
| 2021/0307672 | A1 | 10/2021 | Elwood et al. |
| 2022/0031248 | A1 | 2/2022 | Grant et al. |
| 2023/0062081 | A1 | 3/2023 | Kuperman et al. |
| 2024/0398323 | A1 | 12/2024 | Frankel et al. |
| 2024/0398324 | A1 | 12/2024 | Frankel et al. |
| 2024/0398325 | A1 | 12/2024 | Frankel et al. |
| 2024/0398326 | A1 | 12/2024 | Frankel et al. |
| 2024/0398327 | A1 | 12/2024 | Frankel et al. |

FOREIGN PATENT DOCUMENTS

| | | |
|---|---|---|
| KR | 10-2141185 B1 | 9/2020 |
| WO | WO 2005/109334 A2 | 11/2005 |
| WO | WO 2019/046799 A1 | 3/2019 |

OTHER PUBLICATIONS

Frankel et al., Electrographic Seizure Monitoring with a Novel, Wireless, Single-Channel EEG Sensor. Clin Neurophys Practice. Jan. 1, 2021;6: 172-178.

Frankel et al., Wearable Reduced-Channel EEG System for Remote Seizure Monitoring. Front Neurol. Oct. 18, 2021;12: Article 728484 in 13 pages.

Hirsch et al., American Clinical Neurophysiology Society's Standardized Critical Care EEG Terminology: 2021 Version. J Clin Neurophys. Jan. 1, 2021;38(1): 1-29.

Jia et al., Design of a Wireless EEG System for Point-of-Care Applications. Proc IEEE Annu Northeast Bioeng Conf. Apr. 2013; 2013: 78-79.

Persyst®, Mobile App User Guide. Document No. 6218-02; published Feb. 6, 2023; 89 pages.

Prabhu K.M.M., Window Functions and Their Applications in Signal Processing. ISBN-13:978-1-4665-1583-3; Taylor & Francis; 2014; in 405 pages.

Saputro et al., Seizure Type Classification on EEG Signal using Support Vector Machine. IOP Conf. Series: J Phys Conf. Series (2019) 1201: 012065 in 8 pages.

Scheuer et al., Seizure Detection: Interreader Agreement and Detection Algorithm Assessments Using a Large Dataset. J Clin Neurophys. Sep. 1, 2021;38(5): 439-447.

International Search Report and Written Opinion dated Sep. 9, 2024 for Application No. PCT/US2024/031128; 10 pages.

ADAPTIVE SYSTEMS AND METHODS FOR SEIZURE DETECTION AND CONFIDENCE INDICATION

INCORPORATION BY REFERENCE TO ANY PRIORITY APPLICATIONS

This application claims priority to U.S. Provisional Patent Application No. 63/505,678, filed on Jun. 1, 2023, and U.S. Provisional Patent Application No. 63/511,536, filed on Jun. 30, 2023, each of which is incorporated by reference in its entirety. Any and all applications for which a foreign or domestic priority claim is identified in the Application Data Sheet as filed with the present application are hereby incorporated by reference under 37 CFR 1.57.

STATEMENT REGARDING FEDERALLY SPONSORED R&D

This invention was made with government support under Grant No. R44 NS121562, awarded by awarded by the Department of Health and Human Services. The government has certain rights in the invention.

BACKGROUND

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these electric voltage fields create an electrical reading which electrodes on the person's head are able to detect and record. The monitoring of the amplitude and temporal dynamics of the electrical signals provides information about the underlying neural activity and medical conditions of the person.

There are thousands of hospitals across the United States. Many of these hospitals are community or rural hospitals. These community or rural hospitals conventionally are part of a hospital system or network. An example of one such network includes several community hospitals with one major tertiary hospital. A community or rural hospital outside of any large hospital network would typically contract with a large tertiary hospital for emergent and intensive-care solutions outside of the areas of expertise of the community or rural hospital.

EEG monitoring is conventionally only available in the large tertiary hospitals that support a neurology department with an EEG service. Many hospitals do not offer EEG monitoring. These hospitals make arrangements with larger tertiary hospitals or their partners when such monitoring is required or desirable for patients. This conventionally takes the form of a referral of the patient to the tertiary hospital for expert of specialist services. Often this includes travel or transport of the patient to the tertiary hospital for services. This creates many problems particularly for patients in rural areas. As a result, it is desirable to provide improvements in EEG monitoring systems and methods.

SUMMARY

An EEG can be performed to diagnose epilepsy, verify problems with loss of consciousness or dementia, verify brain activity for a person in a coma, study sleep disorders, monitor brain activity during surgery, and monitor additional physical problems. An appropriate treatment plan can be developed based on the EEG.

Disclosed herein are systems, methods, and computer-readable media for monitoring brain activity using one or more wireless EEG sensors configured to be removably placed in one or more locations on a scalp of a patient. One or more computing devices can communicate with the EEG sensors and facilitate setting up the EEG sensors, receiving, and processing EEG data collected by the EEG sensors. Advantageously, accurate EEG measurements can be obtained and processed to determine (and treat) one or more physiological conditions of a patient, such as seizures, epilepsy, or the like. In addition, disclosed systems and methods allow non-experts to set-up EEG monitoring so that a much larger patient population can benefit from the monitoring.

BRIEF DESCRIPTION OF THE DRAWINGS

In the following description, various implementations will be described. For purposes of explanation, specific configurations and details are set forth in order to provide a thorough understanding of the implementations. However, it will also be apparent to one skilled in the art that the implementations may be practiced without the specific details. Furthermore, well-known features may be omitted or simplified in order not to obscure the implementation being described.

DETAILED DESCRIPTION

Overview

Certain EEG monitoring systems can include complicated multi-component medical device systems, which require technical skill for set-up and coordination and can be uncomfortable for the wearer. When such systems are used outside of a large or research hospital with special expertise, set-up and coordination can be difficult and prone to user error. EEG monitoring systems which use multiple sensor components also require time synchronization across individual devices in order to combine sensor data. When the sensors are not wired together, achieving time synchronization across multiple sensor devices can be difficult to achieve. EEG monitoring systems may also be used for long-term use, either at home or in a hospital of any given size or specialty including, for example, small general hospitals in rural areas. Long-term EEG recording requires a high level of complexity in set up and coordination but needs to be seamless and simple for day-to-day use.

Described herein are improved systems, kits, and methods for EEG monitoring and seizure detection.

Wearable Sensors and EEG Monitoring Kit

Figure 1A:
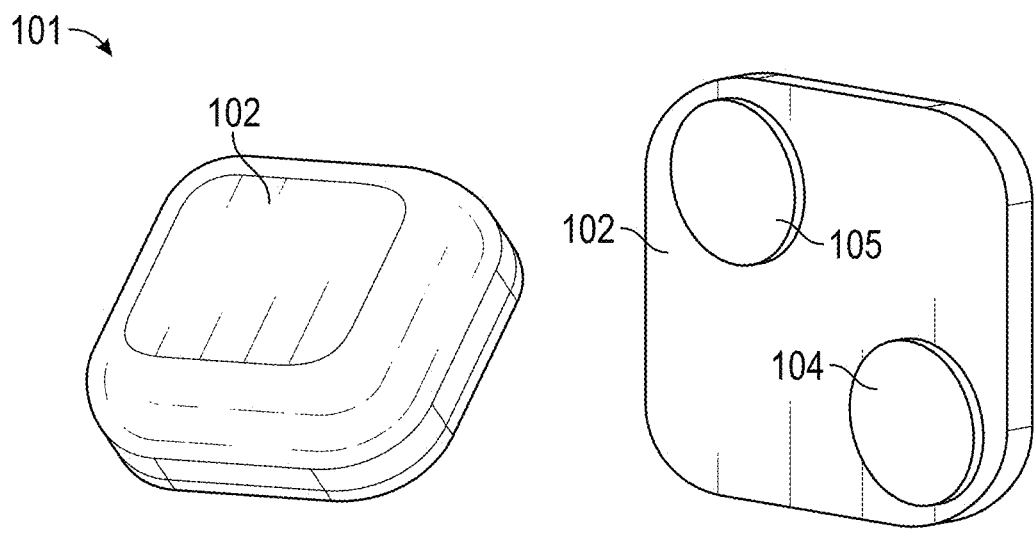
FIG. 1A is a perspective top view and bottom view illustration of an EEG recording wearable sensor.

FIG. 1A is a perspective top view and bottom view illustration of an EEG recording wearable sensor 101, which can be used as a seizure monitoring tool. As shown in FIG. 1A, the wearable sensor 101 is self-contained in a housing 102. The housing 102 may be formed of a plastic, polymer, composite, or the like that is water-resistant, waterproof, or the like.

The housing 102 can contain all of the electronics for recording EEG from at least two electrodes 104, 105. The electrodes 104, 105 are on the bottom, or scalp facing, side shown on the right side of FIG. 1A. Electrodes 104, 105 may be formed of any suitable material. For example, electrodes 104, 105 may comprise gold, silver, silver-silver chloride, earbon, combinations of the foregoing, or the like. One of the electrodes 104, 105 can be a reference electrode and the other can be a measurement (or measuring) electrode. As noted above, the entire wearable sensor 101 may be self-contained in a watertight housing 102. The wearable sensor 101 can be designed to be a self-contained EEG machine that is one-time limited use per user and disposable. The wearable sensor 101 can include more than two electrodes. In some cases, the wearable sensor 101 includes three electrodes. In some implementations, the wearable sensor 101 includes four electrodes. Additional electrodes (such as a third and/or fourth electrode) may be formed of any suitable material, for example gold, silver, silver-silver chloride, carbon, combinations of the foregoing, or the like. In some implementations, the wearable sensor 101 may include additional sensors such as an accelerometer, a PPG sensor, a differential PPG sensor, a skin chemistry sensor, a temperature sensor, etc.

The wearable sensor 101 has two electrodes 104, 105 and can be used alone or in combination with other wearable sensors 101 (such as, three other wearable sensors 101) as a discrete tool to monitor seizures (and in some cases count seizures). It may be desirable, but not necessary, that the user has had a previous diagnosis of a seizure disorder using a traditional wired EEG based on the 10-20 montage. This diagnosis provides clinical guidance as to the most optimal location to place the wearable sensor 101 for recording electrographic seizure activity (sometimes referred to as seizure activity) in an individual user. In some cases, the electrode 104, 105 spacing uses a bipolar derivation to form a single channel of EEG data.

Figure 1B:
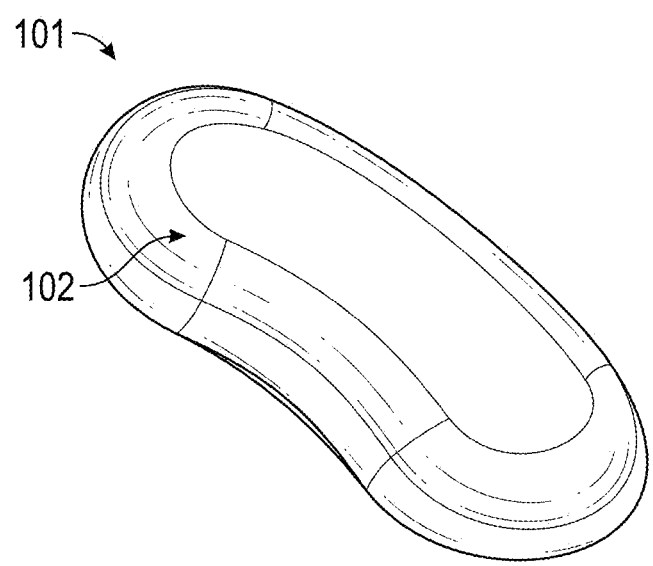
FIGS. 1B to 1D are various views of an EEG recording wearable sensor.

FIG. 1B is a perspective top view illustration of an EEG recording wearable sensor 101 with a housing 102 that has an extended, rounded shape. Such shape can be referred to as a jellybean shape, and may facilitate accurate placement on a subject (or patient) in a correct orientation as well as promote patient comfort and prolonged wear.

Figure 1C:
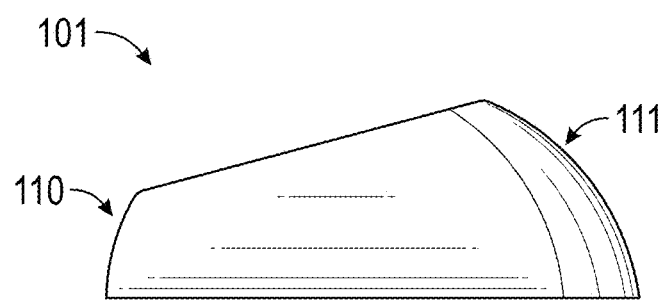
Figure 1D:
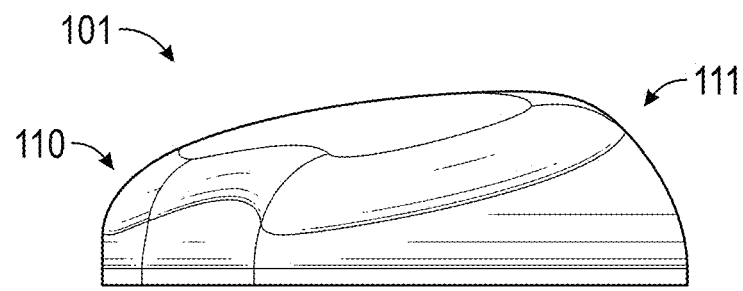

In some cases, the EEG recording wearable sensor 101 is shaped to fit behind the ear. The EEG recording wearable sensor 101 can be shaped to fit along the hairline. The EEG recording wearable sensor 101 can be shaped to fit along a scalp. For example, as shown in FIG. 1B, the EEG recording wearable sensor 101 has an extended rounded shape which is configured to fit around or complement a hairline of a user, such that the extended, rounded shape of the housing 102 facilitates unobtrusive wear of the sensor on the scalp of the user while facilitating collection of the EEG signals. In some implementations, the housing 102 includes a narrow portion configured to curve around the hairline of a user. FIG. 1C provides a cross-sectional view, and FIG. 1D provides a perspective view of the EEG recording wearable sensor 101 of FIG. 1B. FIG. 1C-1D illustrate that the housing 102 includes a narrow portion 110. The side of the housing 102 with the narrow portion 110 can be positioned closer to the patient's ear (see FIG. 2C), which can facilitate unobtrusive wear and collection of the EEG signals. The narrow portion 110 can be thinner than other parts of the housing 102. The housing 102 can become thicker (or widen) from the end that includes the narrow portion 110 to the opposite end 111. Such varying thickness of the housing 102 can facilitate unobtrusive wear. Thickness of the housing 102 in the widest portion can be about 10.0 mm, 9.5 mm, 9.0 mm, 8.5 mm, 8.0 mm, 7.5 mm, 7.0 mm, 6.5 mm, 6.0 mm, 5.5 mm, 5.0 mm, 4.5 mm, 4.0 mm, or within a range constructed from any of the aforementioned values.

In some implementations, the EEG recording wearable sensor 101 is shaped to mimic the look of hearing aids. The EEG recording wearable sensor 101 can include an antenna. The external design (jellybean shape) of the EEG recording wearable sensor 101 can influence the internal shape, requiring unique design and tuning of the antenna.

In some cases, the EEG recording wearable sensor 101 includes a power source supported by the housing and configured to provide power to the electronic circuitry. In some cases, the EEG recording wearable sensor 101 includes a rechargeable battery. The EEG recording wearable sensor 101 can includes electrode. The EEG recording wearable sensor 101 can include at least two electrodes positioned on an exterior surface of the housing and configured to detect EEG signals indicative of a brain activity of the user when the housing is positioned on a scalp of the user. The electrodes may be disposed within the housing 102 of the EEG recording wearable sensor 101. Unlike traditional wired EEG systems employing the 10-20 montage, the EEG recording wearable sensor 101 can allow a much smaller spacing between the measurement and reference electrodes, which may not only make the housing 102 more compact, but also improve signal quality. The distance between the electrodes can be configured to allow for less noisy EEG signal capture, thus improving signal quality.

The distance between the electrodes can be reduced, particularly when compared to traditional wired EEG systems employing the 10-10 or 10-20 montage. The distance between electrodes can be no more than about 25 mm center to center, no more than about 20 mm center to center, no more than about 18 mm center to center, no more than about 15 mm center to center, no more than about 10 mm center to center, or within a range constructed from any of the aforementioned values. The housing 102 can be configured so that the electrodes are disposed at a distance configured to allow better EEG signal capture.

The EEG recording wearable sensor 101 includes an electronic circuitry that may be supported by the housing 102. The electronic circuitry can be configured to process the EEG signals detected by the at least two electrodes. In some implementations, the electronic circuitry is configured to wirelessly communicate processed EEG signal to a remote computing device. The remote computing device can be a portable computing device as described herein.

An extended, rounded shape for an EEG recording wearable sensor 101 may allow an EEG recording wearable sensor 101 to provide: (a) proper electrode pair spacing to allow EEG signal capture; (b) an enclosed housing 102 large enough to contain a full electronics package, including an antenna and a battery that supports frequent communication (such as, Bluetooth or Bluetooth low energy (BLE)); and/or (c) a housing 102 design that complements the curvature around a scalp and/or a hairline and/or behind ears.

In some cases, the surface area of the housing 102 is about 8.5 $cm^2$, 8.0 $cm^2$, 7.5 $cm^2$, 7.0 $cm^2$, 6.5 $cm^2$, 6.0 $cm^2$, 5.5 $cm^2$, 5.0 $cm^2$, 4.5 $cm^2$, or within a range constructed from any of the aforementioned values. The surface area of the jellybean shaped housing 102 illustrated in FIG. 1B can be about 20 $cm^2$, 19.5 $cm^2$, 19.0 $cm^2$, 18.5 $cm^2$, 18.0 $cm^2$, 17.5 $cm^2$, 17.0 $cm^2$, 16.5 $cm^2$, 16.0 $cm^2$, 15.5 $cm^2$, 15.0 $cm^2$, 14.5 $cm^2$, 14.0 $cm^2$, 13.5 $cm^2$, 13.0 $cm^2$, 12.5 $cm^2$, 12.0 $cm^2$, 11.5 $cm^2$, 11.0 $cm^2$, 10.5 $cm^2$, 10.0 $cm^2$, 9.5 $cm^2$, 9.0 $cm^2$, 8.5 $cm^2$, 8.0 $cm^2$, 7.5 $cm^2$, 7.0 $cm^2$, 6.5 $cm^2$, 6.0 $cm^2$, 5.5 $cm^2$, 5.0 $cm^2$, 4.5 $cm^2$ or less, or within a range constructed from any of the aforementioned values. The volume of the jellybean shaped housing 102 illustrated in FIG. 1B can be about 8.0 $cm^3$, 7.5 $cm^3$, 7.0 $cm^3$, 6.5 $cm^3$, 6.0 $cm^3$, 5.0 $cm^3$, 4.5 $cm^3$, 4.0 $cm^3$, 3.5 $cm^3$, 3.0 $cm^3$, 2.5 $cm^3$, 2.0 $cm^3$ or less, or within a range constructed from any of the aforementioned values. The wearable sensor 101 can be placed anywhere on the scalp of a patient to record EEG (such as, behind the ear).

The wearable sensor 101 may be packaged such that removal from the package activates the circuitry. Implementations of the wearable sensor 101 can be placed anywhere on the scalp as placing a conventional wired EEG electrode. The wearable sensor 101 can self-adhere to the scalp either through a conductive attachment, an attachment with a conductive, and/or through mechanical means such as intradermal fixation with a memory-shape metal, or the like.

Once attached to the scalp (for instance, with an attachment as described below), some implementations enable the wearable sensor 101 to perform as seizure detection device (alone or in combination with one or more other wearable sensors 101, such as three other wearable sensors 101). The wearable sensor 101 can record EEG continuously, uninterrupted for up to sixteen (or more) days. In some implementations, each EEG recording wearable sensor 101 is configured to detect EEG signals independent of the other sensors.

The wearable sensor 101 may employ capacitive coupling as a means to spot-check signal quality. A handheld, or other device, can be brought near the wearable sensor 101 to capacitively couple with the device as a means to interrogate the EEG or impedance signal in real time. The wearable sensor 101 may be used to alert to seizures in real time, or near real time.

The wearable sensor 101 could be used to record ultra-low frequency events from the scalp such as cortical spreading depressions. Amplifier circuitry (not shown) may be appropriate for recording DC signals. Alternatively, the amplifier circuitry may be appropriate for recording both DC and AC signals. The wearable sensor 101 may be used after a suspected stroke event as a means to monitor for the presence or absence of cortical spreading depressions and/or seizures or other epileptiform activity. The wearable sensor 101 may be placed on the scalp of a patient by any type of health care provider such as an emergency medical technician, medical doctor, nurse, or the like.

In some implementations, the wearable sensor 101 may employ capacitive coupling to monitor for cortical spreading depressions in real time. The spreading depressions could be analyzed over time and displayed as a visualization of the EEG. The wearable sensor 101 may store these EEG (such as, in storage) for later retrieval. These EEG could also be archived in electronic medical records, or the like.

Figure 2A:
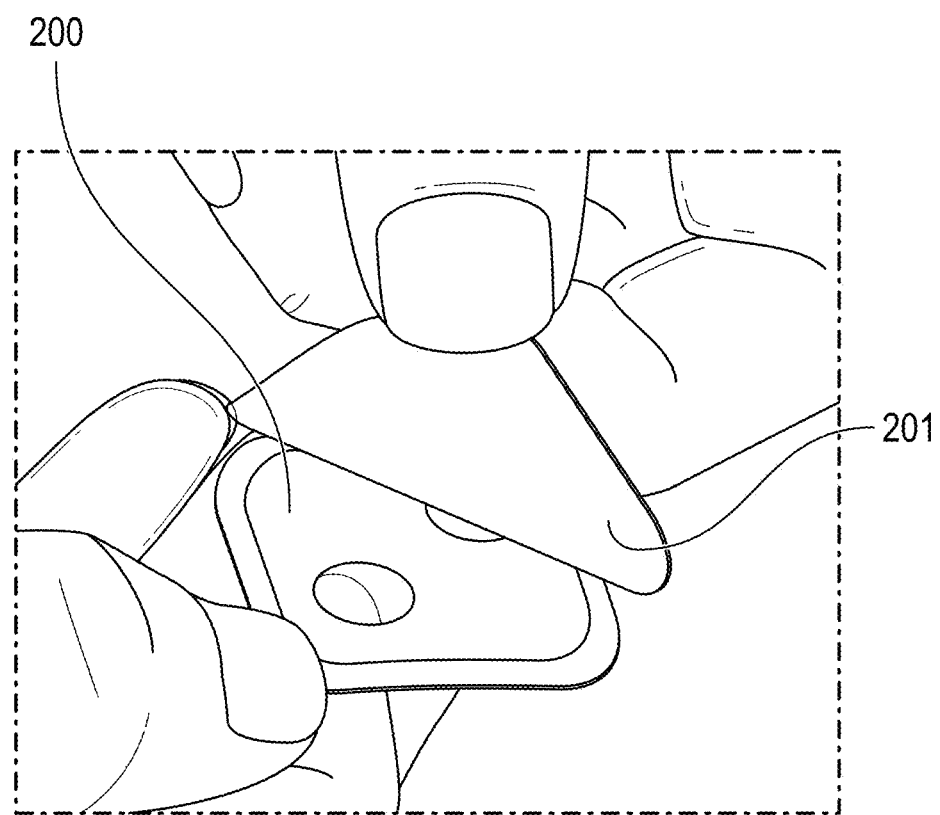
FIG. 2A illustrates an example attachment.
Figure 2B:
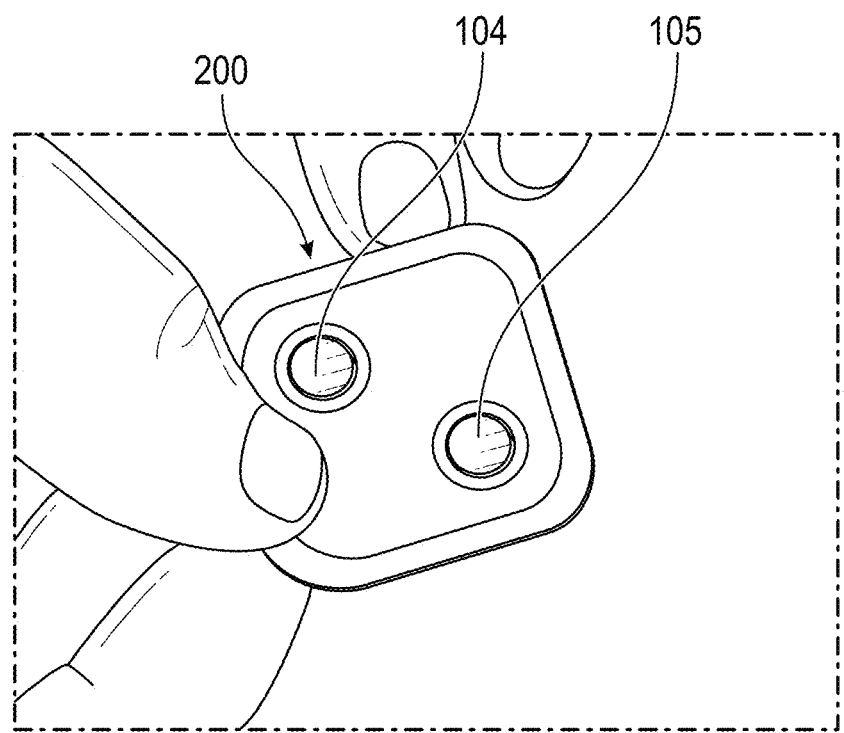
FIG. 2B illustrates an example attachment placed onto the wearable sensor, aligned over the electrodes.

FIG. 2A depicts an attachment 200 being peeled off a backing 201 to reveal an adhesive side. The attachment 200 can be referred to as a sticker or adhesive. The backing 201 may be made of paper, plastic, or any other suitable material. FIG. 2B depicts the attachment 200 placed onto the wearable sensor 101, aligned over the electrodes 104, 105. In some cases, the attachment includes a first side shaped to substantially match the extended, rounded shape and configured to be attached to the exterior surface of the housing 102 of the wearable sensor 101. In some implementations, the attachment includes a second side configured to removably position the wearable sensor 101 on the scalp of a user. A layered attachment 200 may be utilized, which is provided to a user that may remove a layer (the backing 201) to expose an adhesive containing the hydrogel in wells aligned with the positioning of the electrodes (such as electrodes 104, 105). The attachment may then be placed on the sensor, (sensor 101) and thereafter on the user's skin to adhere sensors such as sensor 101 to the user's skin. Even though the attachment 200 may be illustrated as having rectangular shape, in any of the implementations disclosed herein, the attachment 200 can have a jellybean shape that matches the shape of the housing 102 illustrated in FIG. 1B, and the like.

Figure 2C:
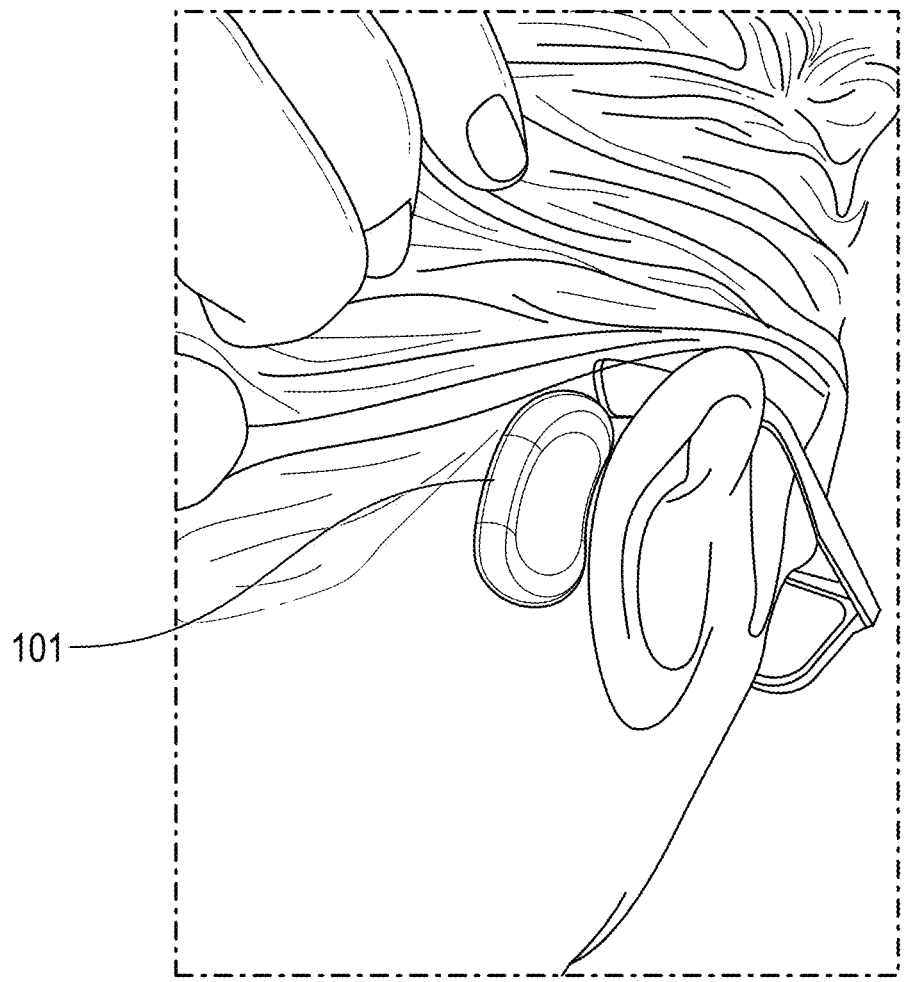
FIG. 2C illustrates an example sensor placed onto a patient's scalp.

FIG. 2C illustrates a sensor 101 placed onto a patient's scalp. The sensor 101 is reversibly attached to the scalp with the attachment 200. The sensor 101 is located at an appropriate place on the user, for example, on the scalp below the hairline, in order to sense and record EEG data. The EEG data may be analyzed on-board, for example, via application of an analysis or machine learning model stored in the sensor 101 or may be analyzed by a local device or remote device or a combination of the foregoing. By way of example, the sensor 101 may communicate using a wired or wireless protocol, for example, secure Bluetooth Low Energy (BLE), to a local device using a personal area network (PAN), such as communicating data to a smartphone or a tablet. Similarly, the sensor 101 may communicate with a remote device using a wide area network (WAN), such as communicating EEG data to a remote server or cloud server over the Internet, with or without communicating via an intermediary device such as a local device.

The hydrogel is conductive and also provides enough adhesion to the scalp for effective recording of EEG for long wear times. Alternatively, the wearable sensor 101 may be adhered with a combination conductive hydrogel with an adhesive construct. After use, the attachment 200 can simply be peeled off the wearable sensor 101 and thrown away. Prior to the next use (for example after a wear period), a new attachment 200 can be applied to the wearable sensor 101.

Consistent EEG signal data from person-to-person is made possible by using a one-piece converted conductive hydrogel and adhesive construct attachment 200. The attachment 200 enables reversable adhesion of the wearable sensor 101 to the scalp. The design of the attachment 200 also reduces both water infiltration and water evaporation from the hydrogel during long wear times. In some cases, the attachment 200 is made by laminating a number of adhesive and non-adhesive layers with wells filled with a hydrogel and sandwiched between release liners. In some implementations, the attachment 200 is further packaged individually in air-tight and water-tight pouches.

EEG System Setup and Provisioning

The systems and methods provided herein can include software to assist a user in setting up the system. The user may be a healthcare provider or a patient.

Figure 3:
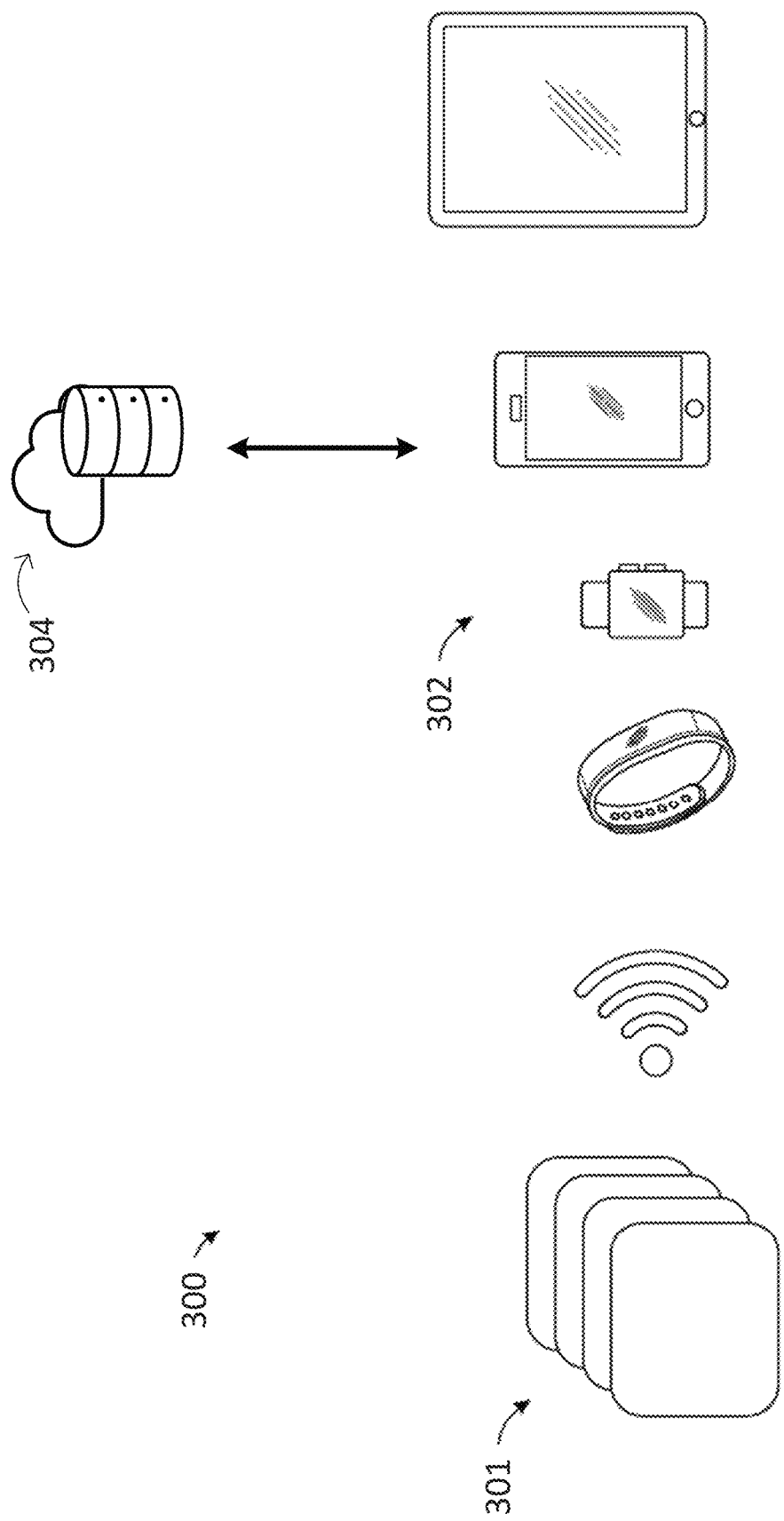
FIG. 3 is an illustration of an EEG monitoring system.

FIG. 3 is an illustration of an EEG monitoring system 300. The system of FIG. 3 includes a plurality of wearable sensors 301 configured to record a brain activity of a patient. Each wearable sensor 301 can include at least two electrodes configured to detect signals indicative of the brain activity of the user when the wearable sensor is positioned on a scalp of the user. Each wearable sensor 301 can further includes an electronic circuitry configured to, based on the signals detected by the at least two electrodes, determine data associated with the brain activity of the user and wirelessly transmit the data associated with the brain activity of the user to one or more portable computing devices 302. Any of the wearable sensors 301 can be the wearable sensor 101.

In some cases, the system further includes a non-transitory computer readable medium storing instructions that, when executed by at least one processor the one or more portable computing devices 302, cause the at least one processor to facilitate activation of the plurality of wearable sensors 301; instruct the user to position the plurality of wearable sensors 301 on the scalp of the user using a plurality of attachments configured to removable attach the plurality of wearable sensors 301 to the scalp of the user; and record the data associated with the brain activity of the user transmitted by the plurality of wearable sensors 301.

The portable computing device 302 can include communication functionality, such as wireless communication functionality. The portable computing device 302 can be configured for being worn by the user. The portable computing device 302 can include a smartwatch, which may have a display. The portable computing device can 302 can include a smart band, smart jewelry, or the like, which may not have a display. The portable computing device 302 can include a tablet or another computing device, such as medical grade tablet. Such portable computing device 302 may include a display that is larger than the display of a smartwatch. The portable computing device 302 may connect to a remote computing device 304 (which can be a cloud service) through a network, such as the Internet. The remote computing device 304 can include one or more computing devices, such as servers.

Provided herein are systems for monitoring brain activity. In some implementations, the systems include a plurality of wearable sensors 301 configured to detect EEG signals indicative of a brain activity of a patient. Each wearable sensor of the plurality of wearable sensors 301 can include at least two electrodes configured to monitor the EEG signals when the wearable sensor is positioned on a scalp of the patient. Each wearable sensor of the plurality of wearable sensors 301 can include an electronic circuitry configured to process the EEG signals monitored by the at least two electrodes. In some cases, systems described herein further include a non-transitory computer readable medium storing executable instructions which may be executed by at least one processor of a portable computing device 302.

Patient EEG data collected by the plurality of wearable sensors 301 may include a plurality of EEG data channels. Each wearable sensor can include two electrodes, which may interchangeably serve as a discrete sensing electrode and a discrete reference electrode for each wireless EEG sensor. The wearable sensors may measure a differential voltage between the discrete sensing electrode and the discrete reference electrode. The differential voltage may be measured temporally, creating an EEG data channel for each sensor of the plurality of discrete wireless EEG sensors. The resulting plurality of EEG data channels may be provided to one or more portable computing devices, such as the portable computing devices 302 and processed as patient EEG data. In some implementations, the discrete wireless EEG sensors may collect the patient EEG data independently and without reference to one another. Each EEG sensor may independently provide the EEG data channel to one or more portable computing devices where the plurality of EEG data channels may be compiled to form patient EEG data.

Seizure Detection Pathway for EEG Data Collection and Processing

Approaches described herein can detect and output possible or potential electrographic seizure events (sometimes referred to as seizure events). This can be applicable for one or more of 1) rapid detection of an ongoing or recent seizure event or 2) analysis of EEG data ex post facto to detect a seizure event that had occurred in the past. Advantageously, rapid detection can assist a non-specialist clinician to treat a patient, and ex post facto detection can assist a specialist clinician with review of EEG data. Rapid detection can determine a prevalence of EEG data indicative of an electrographic seizure over a duration of time and can be used to output an ongoing or recent (such as, delayed by seconds or several minutes) seizure event. For example, one-minute segments of EEG data can be analyzed on a rolling basis, and a seizure event can be detected in response to identifying presence of a particular electrographic seizure characteristic(s) or pattern(s) X % (such as, 1% or more, 10% or more, 50% or more, or 90% or more) of the time. X can be referred to as a prevalence threshold. Ex post facto seizure detection can output a discrete seizure event (or a whole seizure event), which can refer to a pattern of persistent ictal activity with defined start and stop times. Either rapid or ex post facto detection can provide notification of a seizure event, such as an alert or alarm.

Figure 4A:
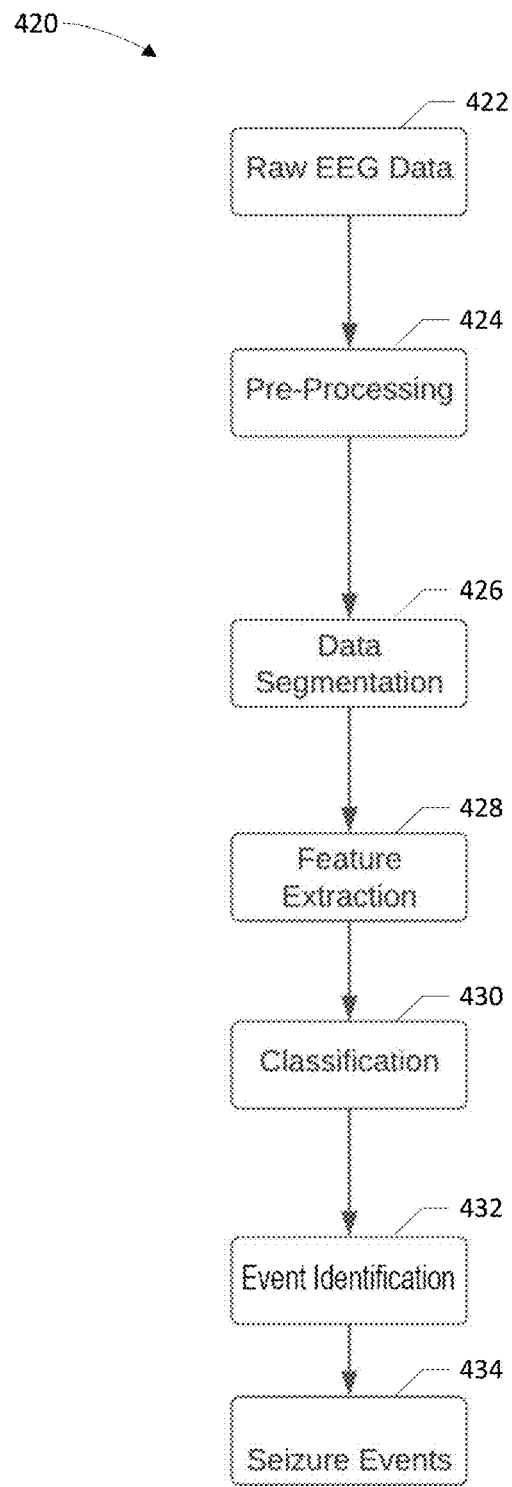
FIGS. 4A-4B illustrate example processes for seizure detection.

A seizure detection pathway can be designed and tuned to detect specific electrographic seizure characteristics and output seizure events. A seizure detection pathway can include a set of preprocessing, data-segmentation, feature extraction, classification, and post-processing subsystems, blocks, or steps to determine seizure events. FIG. 4A illustrates an example seizure detection pathway 420. The pathway 420 can be executed by one or more computing devices, such as by the remote computing device 304 alone or in combination with the one or more portable computing devices 302 or wearable sensors 301. The seizure detection pathway 420 may include more or fewer blocks. One or more of the blocks may be performed in a different order or simultaneously with respect to one or more of the other blocks of process seizure detection pathway 420.

In block 422, the seizure detection pathway 420 can receive EEG data collected by a plurality of EEG sensors, such as the plurality of discrete wireless sensors 301. In some implementations, the EEG data may include four EEG data channels collected by four discrete EEG sensors. These EEG sensors may be placed on the scalp of a patient at four discrete locations (such as, locations corresponding to the left and right frontal and temporoparietal areas). Each data channel may include a number of samples (such as, N) associated with voltage in a particular range of voltages (such as, +/−0.2 millivolts (mV) or +/−0.5 mV).

Next, the example seizure detection pathway 420 may move to block 424 where the EEG data is preprocessed. Preprocessing can include filtering of EEG data in undesired frequency ranges. For instance, the EEG data can be low-pass filtered to remove higher frequency components (such as, electromyographic (EMG) artifacts, electromagnetic interference, etc.), high-pass filtered to remove lower-frequency components (such as, DC shifts, base-line wandering, etc.), notch filtered to remove specific frequencies (such as, 60 Hz line noise), and/or band pass filtered to allow only specific desired frequency components (such as, the delta or theta band). Preprocessing can include adaptive standardization to account for different EEG data characteristics between patients and within a particular patient over time (such as, impedance changes resulting from environmental fluctuations, for instance, humidity or temperature change, skin-electrode interface changes such as increased perspiration or reduced sticker adhesion, or other factors such as a moved or rotated sensor during recording, etc.), as described in the section titled "Adaptive Preprocessing." Preprocessing can include desaturation of the EEG data, which can be performed before or after the adaptive standardization. Saturation may be caused by poor attachment of an EEG sensor, interference, movement artifacts, etc. Saturated data at or near minimum and/or maximum data amplitudes can be corrected. For instance, saturated data can be removed and replaced with a linear interpolation between two points on either side of the minimum or maximum amplitude, or with zeros or NaN values. In some cases, one of the goals of preprocessing is to maximize seizure separability while minimizing inter-subject variability.

The seizure detection pathway 420 may move to block 426 where the preprocessed EEG data may be broken up into short, seconds-long segments. The segments may overlap. For instance, the preprocessed EEG data can be divided into a plurality of segments of a uniform segment length (such as, between 1 and 10 seconds, for instance, 1-2 seconds). In some instances, different length segments may be used for dividing the EEG data.

The seizure detection pathway 420 may move to block 428 where a plurality of features may be extracted from each of the plurality of segments. The features can be extracted for each EEG data segment. The features can include one or more of time domain (or temporal) features, frequency domain (or spectral) features, time-frequency features, and complexity domain features. Temporal features may include a minimum value, maximum value, variance, standard deviation, skew, kurtosis, autocorrelation, cross correlation, among others. Spectral features may include a power spectrum in at least one specific frequency band (such as, about 3 Hz or about 5 Hz), relative band powers, spectral mean, spectral variance, spectral skewness etc. Time-frequency domain features can include a sum, mean, or maximum power of wavelet transforms, rhythmicity, among others. Complexity domain features may include compression ratio (for instance, determined using an encoding process), non-linear energy, spectral entropy, sample entropy, permutation entropy, fractal dimension, line length, zero crossing, zero crossing uniformity, decorrelation time, Hjorth complexity, polynomial fit error, etc. In certain implementations, the extracted features may include correlative measurements across two or more EEG data channels, including maximum cross correlation, spectral cosine similarity, etc, as well as state dynamics.

As discussed below in the section titled "Augmentation of Extracted EEG Data Features," the feature extraction block 428 may include augmenting the at least one extracted feature to create a meta-feature, which is described in more detail below. The meta-feature may be created by pooling two or more extracted features.

Feature extraction can include providing a temporal context, such as adding lagged features, adding rolling averages or rolling normalizations of features, or using combinations of different segmentations to extract features.

The seizure detection pathway may move to block 430 where a classifier (such as, a classifier trained by machine learning processes) may assign a probability that a segment of EEG data has been identified as seizure-like. This can be assigned for each segment of the plurality of segments using the plurality of extracted features associated with each segment. For instance, the classifier can be an extra trees classifier, boosted tree classifier, random forest classifier, or gradient boosting classifier. More generally, the classifier can utilize decision trees classification, neural networks classification, nearest neighbor classification, or support-vector machine classification. The probability assigned by the classifier, which may range from 0 to 1 where 0 represents a 0% likelihood that the segment includes EEG data representative of a seizure and 1 represents a 100% likelihood that the segment includes EEG data representative of a seizure (for instance, EEG data indicative of ictal activity). In some cases, the probability value may be a binary output with a first value indicating that no seizure activity has been detected in the segment and a second value indicating that seizure activity has been detected within the segment. For example, 0 may represent no seizure activity, and 1 may indicate that seizure activity has been detected.

As described herein, performance of a classifier may be further improved with the addition of one or more features associated with patient health information, such as clinical symptoms, previous diagnoses, patient demographics, medications, etc. This additional information can be used in any of the other blocks of the seizure detection pathway 420.

The seizure detection pathway 420 may move to block 432 where the segment probabilities may be combined. Combining segment probability may be referred to herein as event identification, event segmentation, or stitching. An event identifier (or event segmenter, event combiner, or stitcher) can combine temporal sequences of probability values determined by a classifier to output a label representing the presence of a temporally extended seizure phenomena. The output of an event identifier may be any label derived from a temporally extended phenomenon existing across individual temporal segments. A label can indicate, for instance, that a discrete seizure event has started, that a discrete seizure event has been detected from start to end, a start time of a discrete seizure event, a stop time of a discrete seizure event, or that a prevalence of EEG characteristic or pattern has been detected. In some cases, prevalence can be categorized based on, for example, ACNS Critical Care EEG Guideline. For instance, prevalence of at least 10% can be categorized as "Frequent," prevalence of at least 50% can be categorized as "Abundant," and prevalence of at least 90% can be categorized as "Continuous." One or more labels output by an event identifier can assist with the interpretation of EEG data ex post facto or with rapid detection of an ongoing or recent seizure event.

An event identifier can be a pipeline of one or more mathematical operations (or transformations) that use probability values of neighboring temporal segments to determine a new value for a given segment or set of segments in time (such new value is not necessarily a probability). For instance, transformations can include convolutions or filters (such as, tuned filters), smoothing, thresholds, averaging (such as, exponential averaging or moving averaging), or morphological processing. The use of tuned filters can involve convolving a finite vector with either the probability outputs or the thresholded outputs, where the elements of the vector are optimized to increase sensitivity (or true positive rate) and decrease false positive rate, as described herein.

Transformations can take in as input a sequence of probability values and output the presence or absence of a seizure event and which temporal segments belong to that temporally contiguous event. The sequence of steps performed by transformations may be defined by a set of parameters, which can ultimately determine what sort of strings of probability values an event identifier will identify as belonging to a seizure event. A given parameterization of an event identifier can provide a different interpretation of probability values as part or not part of an event. A search across many different parameterizations can be performed in order to find event identifiers that provide accurate interpretations offering optimal tradeoffs between detections and errors. Many different event identifiers can be generated with many different parameterizations, and such event identifiers can be executed to generate events (or labels) from training data. Subsequently, it can be determined which of the event identifiers most frequently predict events that are identifiable as true events in the data while minimizing the number of false identifications. During training of a seizure detection pathway, many different event identifiers can be generated in order to select a subset that may provide an acceptable tradeoff between detections and errors, as described in the section titled "Event Identification and Confidence."

This can be utilized to determine a confidence value associated with the seizure event or label. Additional details of event identification are described herein, such as in the sections titled "Identifying Seizure Events" and "Event Identification and Confidence."

The seizure detection pathway 420 may move to block 434 where a notification of the seizure event may be provided to a user, such as a patient or physician. The notification of the seizure detection event can be provided as a report alarm, or alert. In case of ex post facto detection of a discrete seizure event, this can include a seizure event start time and a stop time and/or duration. A confidence value of the seizure event can be output as described herein.

In some implementations, the seizure detection pathway 420 could be designed and tuned for different product features and/or clinical outcomes. For instance, as described herein, the seizure detection pathway 420 could be designed and tuned for continuous, real-time detection of ongoing or recent seizure activity (rapid detection), which may advantageously provide real-time alerts. An onset of a seizure event could be identified and included in the notifications. In some instances, this may be possible after a sufficient amount of EEG data has been captured and processed.

EEG Data Collection and Processing Using Differentiated Model Pathways

Detection of seizures in the EEG data across different patient types and disease states presents technical problems in the field of EEG monitoring. Seizures present differently across patients, disease states, and seizure types (such as, focal, tonic, clonic, tonic-clonic, absence, subclinical, atonic, or myoclonic), making it difficult to reliably detect and diagnose seizures. Seizures may have one or more electrographic characteristic that differentiates one seizure type or category from another seizure type or category. In order to detect a variety of differentiated electrographic seizure characteristics, a seizure detection process may need to be sufficiently sensitive (or have a high true positive rate). However, as the sensitivity increases, the false positive rate may also increase. False positive rate may be measured by a rate of detection of false positives (or incorrectly identifying a seizure when no seizure is present). Without properly designing and tuning seizure detection processes across diverse patient populations, detection may suffer from high rates of errors due to, for instance, high sensitivity with high false positive rate or low sensitivity with low false positive rate. Advantageously, disclosed implementations of seizure detection can effectively and efficiently detect seizures with high sensitivity and without exceeding a permissible false positive rate across different patient types and disease states. In some instances, disclosed implementations detect seizure events with a sensitivity of at least about 80% and a false positive rate of no more than about 0.21 false positives per hour (or in some cases no more than 0.08 false positives per hour).

The electrographic nature of the seizures (as recorded using EEG) can vary widely. Some seizures may manifest with lower-frequency spike (such as, at around 3 Hz) and slow-waves, such as, which can be indicative of absence-typical seizures. Other seizures may manifest with evolving bursting activity from a continuous state to an on/off state, which can be indicative of tonic-clonic seizures. Yet other seizures can manifest with a poly spike and slow-wave, low-frequency rhythmicity (or sometimes mid-frequency rhythmicity, such as around 10 Hz), slowing in the frequency bands, increase in the mid-frequency bands, or higher-frequency spiking, which can be indicative of focal seizures. Yet other seizures can manifest with singular or repetitive clonus spikes, which can be indicative of myoclonic seizures. Yet other seizures can manifest with on/off bursting activity (and sometimes with high EMG activity), which can be indicative of clonic seizures. Yet other seizures can manifest with solid bursting activity (sometimes with spiking and/or high EMG activity), which can be indicative of tonic seizures. Yet other seizures can manifest with, which can be indicative of a quiet EEG signal, which can be indicative of atonic seizures. Because of these differences in the specific electrographic seizure characteristics, it is difficult to create a one-size-fits-all seizure detection process that can accurately detect all electrographic seizures. Disclosed implementations solve these problems by utilizing a combination of seizure detection pipelines or pathways each of which is designed and tuned (or trained) to detect one or more specific electrographic seizure characteristics. As a result, the combination of pathways can detect differentiated electrographic characteristics (or differentiated characteristics) of various seizure types across divergent patient populations.

In some implementations, one or more blocks or steps of a seizure detection pathway (such as, the pathway 420) may have one or more parameters tuned for detection of at least one differentiated electrographic seizure characteristic. For instance, a seizure detection pathway can be tuned to detect presence of a lower-frequency spike (such as, about 3 Hz) and slow-wave indicative of an absence seizure. As another example, a seizure detection pathway can be tuned to detect evolving bursting activity from a continuous state to an on/off state indicative of tonic-clonic seizures. Multiple seizure detection pathways can be utilized to detect multiple differentiated electrographic characteristics of different types of seizures. That is, a first seizure detection pathway may be differentiated from a second seizure pathway based on differentiating one or more blocks or parameters designed and tuned for detection of different electrographic characteristics.

Seizure detection algorithms trained to detect seizures without such differentiation may disadvantageously suffer from over-generalization leading to poor sensitivity and poor false positive rate. Disclosed approaches for using a plurality of differentiated seizure detection pathways advantageously facilitate detection of electrographic characteristics of seizure types with high sensitivity and low false positive rate.

Figure 4B:
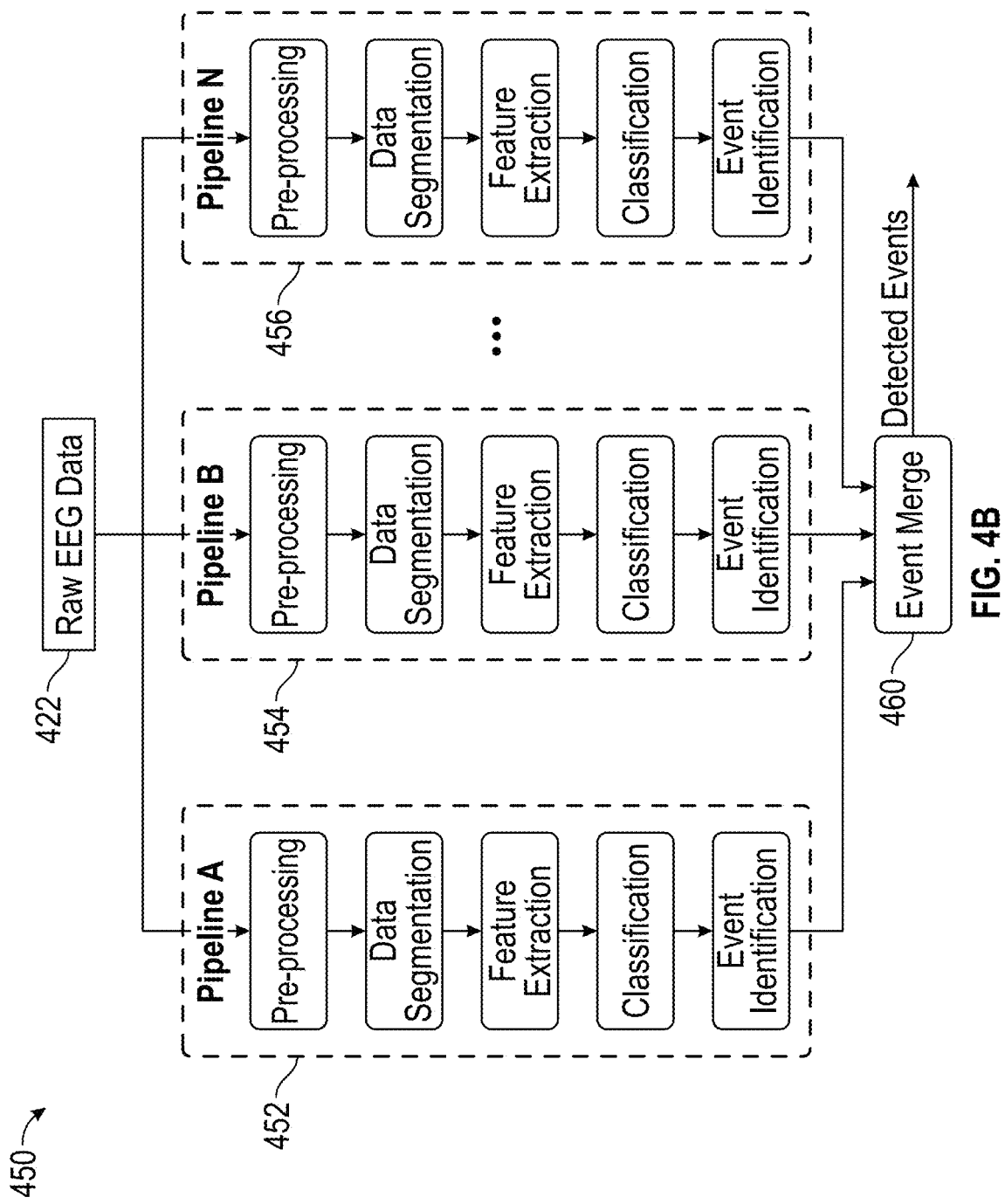

FIG. 4B illustrates a seizure detection process 450 that utilizes multiple seizure detection pathways, including a pathway 452, a pathway 454, and additional one or more pathways 456. Each of the illustrated seizure detection pathways can be similar to the pathway 420 illustrated in FIG. 4A, but the pathways can be differentiated in that the pathways can be designed and tuned to detect electrographic characteristics of different types of seizures. For example, the pathway 452 can be designed and tuned to detect one or more first electrographic characteristics (such as, about 3 Hz spike and slow-waves). As another example, the pathway 454 can be designed and tuned to detect one or more second electrographic characteristics (such as, evolving bursting activity from a continuous state to an on/off state). As yet another example, the pathway 456 can be designed and tuned to detect one or more third electrographic characteristics (such as, mid-frequency rhythmicity). In some instances, another pathway (not shown) may be designed and tuned to detect one or more fourth electrographic characteristics associated with seizure events not included in the pathways 452, 454, and 456. The process 450 can be executed by one or more computing devices, such as by the remote computing device 304 alone or in combination with the one or more portable computing devices 302 or wearable sensors 301.

The plurality of seizure detection pathways may be differentiated at one or more of preprocessing, data segmentation (or segmenting), feature extraction, classification, or event identification. Because each of the pathways is designed and tuned to detect one or more unique electrographic characteristics, the data segmentation may also be unique. As an example of differentiation during data segmentation, the pathway 452 may utilize segments of a shorter length, such as between 1 and 2 seconds, as absence seizures tend to have a shorter duration. The pathways 454 and 456 may utilize segments of a longer length, such as between 1 and 4 seconds. As an example differentiation during classification, the pathway 452 may use a classifier trained with data obtained from known seizure events that have an approximately 3 Hz spike and slow-wave morphology, which may be associated with absence seizures. The pathway 454 may use a classifier trained with data obtained from known seizure events that have evolving bursting activity from a continuous state to on/off states, which may be associated with tonic-clonic seizures. The pathway 456 may use a classifier trained with data obtained from known seizure events that have approximately 10 Hz rhythmicity, which may be associated with focal seizures.

As an example of differentiation during event identification, differentiated event identifiers may create seizure events that have one or more unique electrographic characteristics. As described below in connection with the section "Identifying Seizure Events," event identifiers may utilize filtering, smoothing, gap filling, and reduction to output such seizure events. Because some differentiated electrographic seizures tend to happen in closer time proximity to others, one or more event identifiers of the pathway 452 (designed and tuned to detect one or more characteristics related to low-frequency spike and slow-wave seizures) may fill gaps between individual discrete events that happen relatively close in time (such as, within 15 seconds of each other) to create a single discrete seizure event (or a whole seizure event). One or more event identifiers of the pathway 454 (designed and tuned to detect one or more characteristics related to tonic-clonic seizures) may combine any seizure events found within a wider duration of time (such as, within 30 seconds of each other) to create a single discrete seizure event. One or more event identifiers of the pathway 456 (designed and tuned to detect one or more characteristics related to mid-frequency rhythmicity that may be expected to only happen much farther apart in time) may combine any seizure events found within a wider duration of time (such as, within 1 minute of each other) to create a single discrete seizure event. More generally, event identifiers can be differentiated based on a duration of time between discrete seizure events.

Seizure events output by the seizure detection pathways 452, 454, and 456 can be combined, concatenated, or merged by an event merge block 460 (sometimes referred to as a concatenation block). The event merge block can analyze confidence values (and, in some instances, durations) of the seizure events determined by the respective pathway event identifiers, as described in the section titled "Event Identification and Confidence." For example, a discrete seizure event associated with the highest confidence value may be chosen by the event merge block 460 during ex post facto detection. In case of rapid detection, a label that indicates prevalence of an EEG characteristic or pattern that satisfies a prevalence threshold and has the highest confidence may be chosen by the event merge block 460. If there is no pathway event identifier that outputs a label with such prevalence, a label with the highest confidence may be chosen by the event merge block 460.

A notification of one or more detected seizure events can be provided. The notification can be provided following the event merge block 460. The notification may be provided to a user (such as, a patient or clinician) through the portable computing device 302 or the remote computing device 304. The notification may include information about the seizure event, such as, the start time and a stop time and/or duration of a discrete seizure event along with the confidence. EEG data collected by the plurality of discrete wireless sensors may also be included with the notification.

The seizure detection pathways 452, 454, and 456 may be stored as instructions in a computer readable memory and executed by one or more processors. The seizure detection pathways 452, 454, and 456 may be executed concurrently or sequentially. As another example, a subset of blocks of the seizure detection pathways may be executed in parallel. In some implementations, at least two of the seizure detection pathways 452, 454, and 456 may share some blocks (such blocks can be referred to as undifferentiated blocks). For example, at least two pathways can share the preprocessing block 424. This may be due to the temporal and frequency characteristics of the types of seizures processed by the pathways being similar.

Figure 5:
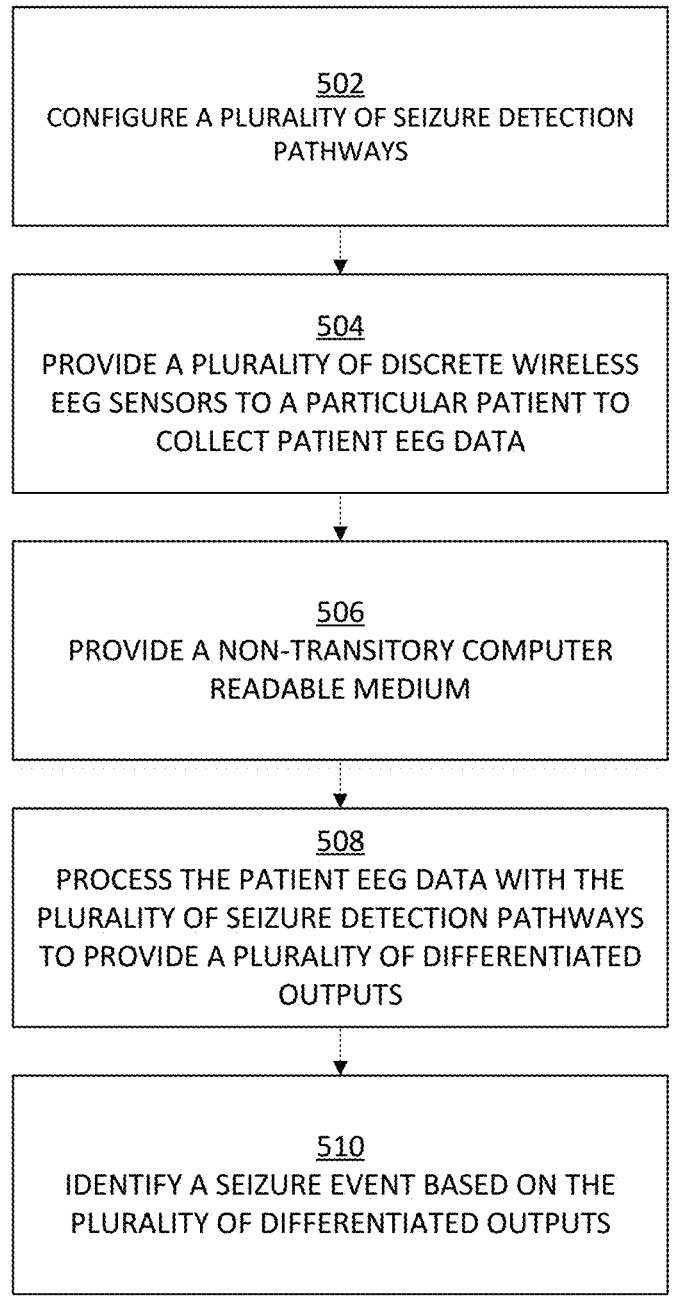
FIG. 5 illustrates an example process for detecting with a seizure event using a plurality of differentiated seizure detection pathways.

FIG. 5 illustrates an example process 500 for detecting differentiated electrographic seizure characteristics using a plurality of seizure detection pathways, such the pathways 452, 454, and one or more additional pathways 456 described in connection with FIG. 4B. The process 500 can be executed by one or more computing devices, such as by the remote computing device 304 alone or in combination with the one or more portable computing devices 302 or wearable sensors 301. The process 500 may include more or fewer steps. One or more of the steps of process 500 may be performed in a different order or simultaneously with respect to one or more of the other steps of process 500. Instructions for executing the process 500 may be stored on a computer readable medium. The instructions may cause one or more processors to perform the step(s) of the process 500. In some cases, the process 500 may include additional or fewer elements. For example, the process may be performed by one seizure detection pathway or three or more seizure detection pathways.

The process 500 may begin at step 502 where a plurality of seizure detection pathways are configured. The plurality of seizure detection pathways may be trained or tuned to detect differentiated electrographic seizure characteristics. The plurality of seizure detection pathways may be trained or tuned using signal processing and/or statistical learning methods on EEG data collected from a patient population. Training data can include EEG data with seizures, EEG data without seizures obtained from subjects who do not experience seizures, and interictal (or in-between-seizures) data from subjects who experience seizures. Training data can be obtained from subjects wearing a plurality of discrete EEG sensors (such as, EEG sensors 301) and/or wired EEG electrodes (such as, positioned according to 10-10 or 10-20 electrode placement).

The plurality of seizure detection pathways may be trained to detect differentiated electrographic seizure characteristics, as described herein. The plurality of seizure detection pathways may be trained to detect absence seizures, focal-onset seizures with clinical convulsions, general-onset seizures without clinical convolutions, bilateral tonic-clonic events, and the like. As described above, each seizure detection pathway may be trained to detect at least one specific electrographic seizure characteristic.

Although certain disclosed examples relate to the detection of seizures, pathways may also be trained to detect strokes, obstructive sleep apnea, or cortical spreading depression in migraine based on the EEG data. Pathways may also be trained to leverage EEG data to determine sleep quality, perform sleep staging, and/or predict Alzheimer's disease, depression, fatigue, multiple sclerosis, Parkinson's disease, or the like. For example, a first seizure detection pathway may be trained to detect electrographic seizure characteristics associated with absence seizures and a second seizure detection pathway may be trained to detect electrographic characteristics associated with Alzheimer's disease.

A seizure detection pathway may be trained to detect at least one electrographic characteristic related to two or more differentiated types of seizures. For example, a first seizure detection pathway may be trained to detect a first characteristic associated with absence seizures, a second seizure detection pathway may be trained to detect a second characteristic related to focal onset seizures, and a third seizure detection pathway may be a hybrid pathway and trained to detect at least one characteristic related to both absence seizures and focal onset seizures. In another example, a third seizure detection pathway may detect a characteristic associated with all types of seizures other than absence seizures and tonic-clonic seizures.

The process 500 may move to step 504 where a plurality of discrete wireless EEG sensors, such as the plurality of EEG sensors 301, may be provided to collect EEG data. As discussed above in conjunction with FIGS. 2A-2C, the sensors may be applied to the scalp of a patient in discrete locations. The plurality of discrete wireless EEG sensors may include four discrete wireless EEG sensors, as described herein. The four EEG sensors may be placed on the scalp of a patient at four discrete locations (such as, locations corresponding to the left and right frontal and temporoparietal areas). For example, a first EEG sensor may be placed on the left forehead of the patient, a second EEG sensor may be placed on the right forehead of the patient, a third EEG sensor may be placed behind a left ear of the patient, and a fourth EEG sensor may be placed behind a right ear of the patient. These locations may correspond with an F7 location, an F8 location, a TP9 location, and a TP10 location respectively. Although process 500 (or any other processes described herein) may be described in relation to data obtained by discrete wireless EEG sensors, the process 500 (or any other process described herein) and seizure detection pathways may be implemented with wired EEG systems. As described herein, the discrete EEG sensors may collect patient EEG data which can include a plurality of EEG data channels.

As described herein, patient health information (or patient information) may be detected or obtained. Patient information may include physiological measurements such as heart rate, temperature, movement, etc., which may be collected by the additional sensors of the discrete wireless EEG sensors or stand-alone additional sensors. Patient information may include information related to the patient's environment such as a time of day, the current weather, current temperature, current humidity, a movement of the patient, etc. Patient information may include clinical symptoms, previous diagnoses, patient demographics, patient medications, time of day, etc. Patient information can be provided by the portable computing device 302. For example, the portable computing device 302 may receive a patient medical history from the remote computing device 304. In another example, the patient may provide patient information to the portable computing device 302 through a user interface. Patient information can be utilized by any of the steps 508 or 510 of the process 500.

The additional sensors may include one or more of the following sensors. A photoplethysmography (PPG) sensor can be used to detect the patient's heart rate, heart rate variability, etc. A differential PPG sensor may be used to detect blood pressure and/or vascular tone. An accelerometer may be used to detect a movement of the patient and/or an orientation. This information may be useful for detecting characteristics associated with motor effects (or muscular contractions), which may be associated with tonic-clonic seizures, or for controlling the orientation of the EEG sensors. A temperature sensor may be used to detect the temperature. Other sensors may be used to detect electrodermal activity, skin chemical composition, temperature, humidity, light, sound, etc. As described herein, information related to environmental conditions (such as, temperature or humidity) can be used to standardize the EEG data, for instance, during preprocessing. Because weather conditions may have an impact on the occurrence of seizures, information related to the weather can be obtained to facilitate seizure detection.

The process 500 may move to step 506 where a non-transitory computer readable medium may be provided. The non-transitory computer readable medium may store instructions for executing a seizure detection process configured to process the EEG data (and patient information, if applicable) using the seizure detection pathways. The instructions may be executed by one or more processors, such as the processor(s) of the one or more portable computing devices 302 and/or the remote computing device 304.

The process 500 may move to step 508 where EEG data is processed with the plurality of seizure detection pathways to provide a plurality of differentiated outputs. As described in connection with FIG. 4B, each seizure detection pathway may include: a preprocessing step, a segmenting step, a feature extraction step, a classification step, and an event identification step. At least one of these steps may be differentiated among the plurality of seizure detection pathways. For example, three seizure detection pathways may be employed, and the steps of the seizure detection pathways may be undifferentiated except for the classification step. The differentiated classification steps of the three seizure detection pathways may be tuned to detect a differentiated electrographic seizure characteristics. In some implementations, two or more steps of the seizure detection pathways may be differentiated.

As described in connection with FIGS. 4A and 4B, the preprocessing step of a seizure detection pathway, such as step 424 of the seizure detection pathway 420, may include one or more of normalizing, standardizing, filtering, denoising, detrending, demeaning, artifact rejection, or desaturation of the EEG data. One or more of these operations or parameters can be differentiated between the seizure detection pathways. The EEG data may be preprocessed as a whole, as individual EEG data channels, or as subgroups of EEG data channels. In some cases, the preprocessing step may be adaptive, as discussed below in the section titled "Adaptive Preprocessing."

The differentiated preprocessing steps of the plurality of seizure detection pathways may standardize the patient EEG data to account for inter-patient differences and within patient differences. Inter-patient differences may include differences between two or more patients such as the difference in skin impedance or skull thickness. Within-patient differences may include differences between skin-electrode interfaces of different electrodes, changes to an individual skin-electrode interface over time, or changes that arise from replacing an electrode, such as placing the new electrode in a slightly different location or orientation from the original. The differentiated preprocessing steps of the plurality of seizure detection pathways may maximize the ability to separate seizure-like data from non-seizure like data in a feature-space (for instance, based on the power in a specific frequency band).

As described in connection with FIGS. 4A and 4B, the segmenting step of a seizure detection pathway, such as step 426 of the seizure detection pathway 420, may include splitting the patient EEG data into a plurality of EEG data segments. The plurality of seizure detection pathways can be differentiated at the segmenting step.

As described in connection with FIGS. 4A and 4B, the feature extraction step of a seizure detection pathway, such as step 428 of the seizure detection pathway 420, may process one or more segments of patient EEG data to extract at least one EEG data feature. In some implementations, the feature extraction step may include retrieving patient information or other contextual information. Patient information may include physiological conditions, demographics, a patient medical history, time of day, etc. Physiological conditions may be measured by the plurality of discrete wireless EEG sensors or one or more other sensors. Contextual information may include a time of day, current weather, or other environmental conditions that the patient may be exposed to. In some cases, patient information, such as a patient medical record or seizure diary, may be retrieved from a remote computing device 304 or via a user interface executed on the portable computing device 302.

In some implementations, the plurality of seizure detection pathways may be differentiated at the feature extraction step. For instance, a first seizure detection pathway may extract at least one feature that is different from the features extracted by a second detection pathway. The differentiated feature may be relevant or useful for detecting a characteristic by the first seizure detection pathway, but irrelevant for detecting a characteristic by the second seizure detection pathway. In some instances, relevant features may be identified through statistical analysis. For example, feature selection methods may be used to identify one or more relevant features for detecting at least one electrographic seizure characteristic. The differentiated pathways may contain a different number of selected features.

In some instances, certain classifiers may perform poorly with an abundance of irrelevant or highly correlated features, while other classifiers may perform well. Reducing the features may improve performance of certain pathways. Feature reduction may be implemented via dimensionality reduction techniques, such as principal component analysis. For example, principal component analysis may be used to reduce 50 features to 3 or 4 principal component dimensions. Feature reduction may also be implemented through feature selection techniques, where the number of features can be specified or determined automatically. Some classifiers may perform poorly with large differences in scale between features and normalizing features may improve performance. Various classifiers may benefit from contextual information as features, for example, patient demographics, time of day, etc.

For example, a low-frequency spike and slow-wave seizure detection pathway (such as, the pathway 452) may extract a power spectral density feature at a particular frequency, such as 3 Hz, but may not extract complexity domain features. A higher-frequency spiking and/or motor effects detection pathway (such as, the pathway 454) may extract different frequency-based metrics. Advantageously, prioritizing relevant features and/or removing immaterial features may increase the sensitivity and decrease the false positive rate. Processor load and memory consumption may also be reduced, thereby increasing the performance of at least one computing device executing the seizure detection pathways.

As described in connection with FIGS. 4A and 4B, the classification step of a seizure detection pathway, such as step 430 of the seizure detection pathway 420, includes assigning a probability value that a segment of EEG data has been identified as seizure-like by a classifier. The probability value may be determined based on at least one feature extracted feature.

The plurality of seizure detection pathways may be differentiated at the classification step. A first seizure detection pathway can use a classifier trained to detect one or more first electrographic seizure characteristics, while a second seizure detection pathway can use a classifier trained to detect one or more second electrographic seizure characteristics. As described above, a classifier used by a particular seizure detection pathway can be trained using EEG data with seizure events that include the particular electrographic seizure characteristic(s) being identified by the pathway.

As described in connection with FIGS. 4A and 4B, the event identification step may include applying one or more event identifiers to the segment probabilities output by the classifier to identify a seizure event. For a discrete seizure event, for instance, an event identifier may identify a start time, stop time, and/or a duration and a confidence value of the seizure event. As described herein, the event identifiers may be differentiated among the seizure detection pathways.

The process 500 may move to step 510 where a seizure event is identified based on the outputs of the plurality of seizure detection pathways. This may be performed by the concatenation or merge step, such as the merge step 460 of FIG. 4B. A notification of the seizure event can also be provided, as described in connection with FIG. 4B.

Advantageously, detection of the one or more seizure events can assist a clinician with determining whether a seizure has occurred and identify the seizure type. The clinician can utilize additional clinical information to make such determination. For instance, determination of an absence seizure can be made responsive to reviewing a notification of the seizure event and information related to patient's condition during the seizure event to verify that at the time of the occurrence of the seizure event the patient experienced a starting spell (or was "absent"). Such information can be imaging data (such as, recorded by a camera) or data recorded by the patient or a third party (for instance, in a diary).

The approaches for detection of the one or more seizure events described herein can facilitate accurate counting and tracking of seizure occurrences, which can assist with effective diagnosis and treatment. For instance, a patient may receive medication adjustments infrequently (such as, every 6 months) based on the patient's tracking of seizure occurrences. The approaches described herein can shorten this period (for instance, to a range of weeks) and facilitate much more frequent review and adjustment of a treatment plan.

Adaptive Preprocessing

Collection of EEG data by a plurality of independent wireless EEG sensors (such as, the sensors 301) positioned at different locations on a patient's scalp may require additional preprocessing to account for expected differences in the EEG data due to within patient differences over time (such as, change in sensor positioning or orientation, sweat, etc.) and due to across patient differences (such as, patient environment temperature, humidity, and sensor orientation). These differences can lead to signal distortion due to impedance and orientation changes that require standardization in support of seizure detection.

Adaptive preprocessing implementations described herein provide technical solutions to address these technical challenges. Advantageously, such implementations may be able to account for the changes in the EEG data in order to effectively process the EEG data using one or more seizure detection pathway approaches described herein, such as those described in connection with FIGS. 4A, 4B, and 5. Adaptive preprocessing can standardize the EEG data to account for changes in the EEG signals monitored by a plurality of independent wireless EEG sensors being worn by a patient. A change can be detected and, responsive to the change, one or more processing parameters can be adjusted to ensure continuity of the EEG data. The changes can be caused by the changes at a skin-sensor interface (such as, due to replacement or degradation of the adhesive), changes in the patient's skin, changes in the environment (such as, the temperature, humidity, etc.), EEG sensor changes (such as, due to sensor replacement, sensor orientation change, movement of the sensor, etc.), changes caused by user activity (such as, perspiration when exercising), or the like.

As described above, preprocessing may include normalizing (such as, containing within a certain range), standardizing (such as, scaling), filtering, denoising, desaturating, and/or modifying the patient EEG data to account for inter-patient and inter-sensor differences. Preprocessing parameters may include parameters used during such operations.

Figure 6:
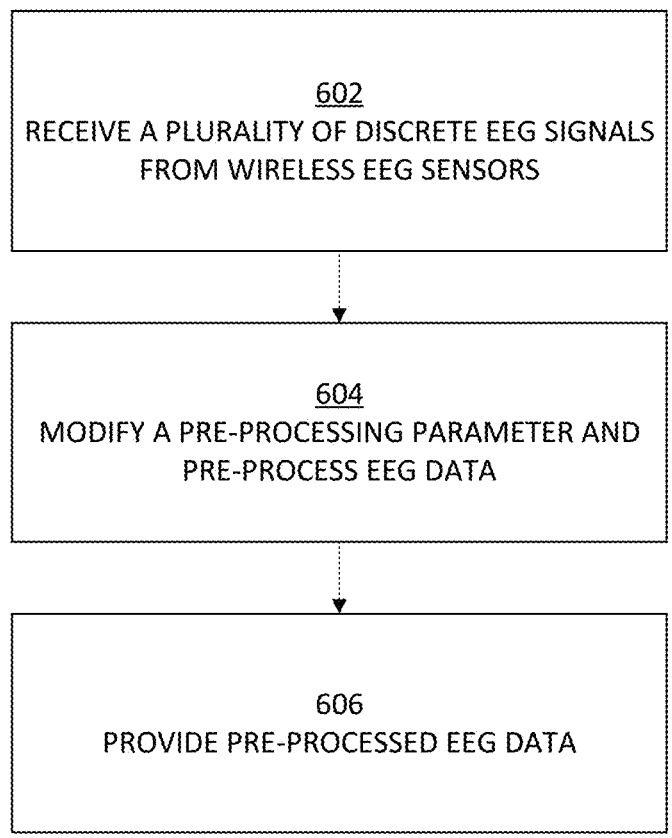
FIG. 6 illustrates an example process for adaptively preprocessing EEG data collected by a plurality of discrete wireless EEG sensors.

FIG. 6 illustrates an example process 600 for adaptively preprocessing EEG data collected by a plurality of discrete wireless EEG sensors, such as the sensors 301. The process 600 can be part of the preprocessing block 424 of FIG. 4A. The process 600 may include more or fewer steps. One or more of the steps of process 600 may be performed in a different order or simultaneously with respect to one or more of the other steps of process 600.

In block 602, the process 600 can receive a plurality of EEG signals (or data) from the plurality of independent wireless EEG sensors. As described herein, the plurality of independent EEG sensors may not share a common reference (such as, a reference electrode). In block 604, the process 600 can modify at least one preprocessing parameter responsive to a change in the EEG signal.

To handle the effects of within or across patient issues in the EEG data, adaptive preprocessing can include adaptively normalizing the EEG data. This can include evaluating variances of windows of EEG data, setting a variance threshold (or scaling factor) as the minimum of identified variance, as the average identified variance, or its square root (i.e., the standard deviation), and normalizing the EEG data by dividing by the variance threshold. The windows can have a duration of 1 second or shorter, 2 seconds, 30 seconds, 1 minute, 2 minutes, 5 minutes, 10 minutes, 30 minutes, an hour or longer. A window can serve as the best estimate of the background baseline noise, and thus can be used to standardize the EEG data in the current window. As an example, let's assume that two-second windows are used. Determined variances of each window of the EEG data can be compared to one another, and the window with the smallest variance can be selected as a so-called "quiet" window that is assumed to include the background noise. A variance threshold can be set to the variance of such quiet window. EEG values in the other windows can be scaled by the variance threshold. Zeroed out or saturated EEG data may not be considered during the variance threshold calculation.

Because the environment of the patient can be highly non-stationary, it may be advantageous to periodically, adaptively update the variance threshold when a new quiet window has not been found after a passage of a duration of time. If a sufficient duration of time has passed without an update to the variance threshold, a growth rate approach can be used in which the current variance threshold is increased by a factor (such as, 5%, 10%, 20%, 30%, 40%, 50%, etc.) until a new quiet window has been identified. The duration of time may be between 1 minute and 1 hour. For example, the duration of time may be 30 seconds, 1 minute, 2 minute, 3 minutes, 4 minutes, 5 minutes, 10 minutes, 15 minutes, 20 minutes, 25 minutes, 30 minutes, 45 minutes, an hour, etc. The variance threshold can be increased continuously (for instance, every minute) until a new quiet window has been identified. The approaches described in this paragraph can be particularly applicable in cases where the variance threshold factor is set to the minimum variance, as described herein.

As described herein, at least one preprocessing parameter may be changed responsive to a change in the EEG sensor position or orientation of an EEG sensor (such as, due to a replacement of the EEG sensor. EEG sensor orientation or replacement may be detected based on an output of an accelerometer or another position and/or orientation measurement sensor. For example, an accelerometer may detect that one of the plurality of discrete wireless EEG sensors has been placed on the patient in an inverted orientation. The accelerometer may detect the change in orientation, and the EEG data received from the inverted EEG sensor may be flipped (such as, multiplied by −1) in the block 604.

The process 600 may move to block 606 where preprocessed EEG data can be provided to the next processing block, such as the data segmentation block of FIG. 4A.

As described herein, adaptive preprocessing approaches can monitor one or more changes in the EEG data and adjust one or more preprocessing parameters responsive to the one or more changes. For instance, adaptive standardization described herein can monitor the EEG data for the occurrence of one or more changes by adaptively updating the variance threshold when a new quiet window has not been found after a passage of a duration of time. Accordingly, a preprocessing parameter (or variance threshold) can be adjusted as a result of not detecting a change in the EEG data over the duration of time. As another example, changes in the positioning or orientation of an EEG sensor can be monitored by a position and/or orientation measurement sensor.

Figure 7:
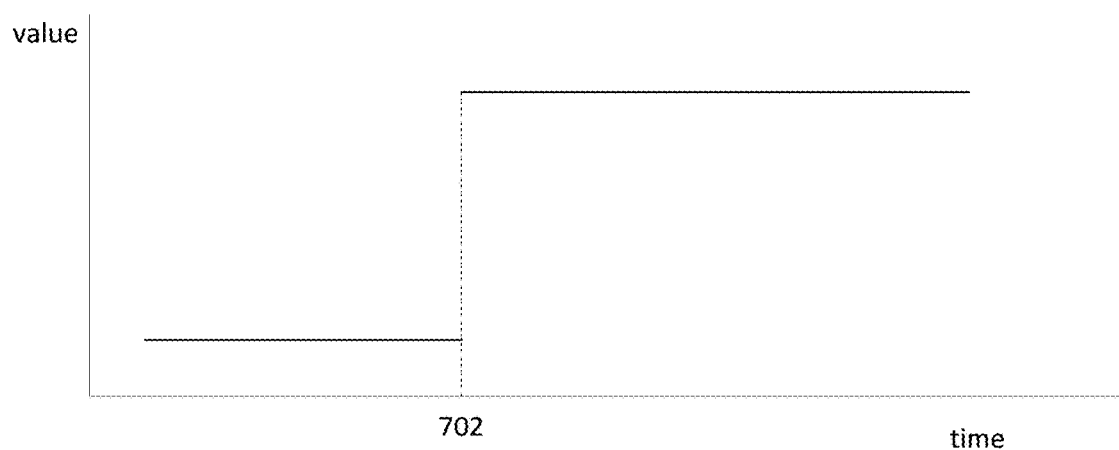
FIG. 7 is an example timeline demonstrating how the process shown in FIG. 6 may be used to adaptively preprocess EEG data collected by the plurality of discrete wireless EEG sensors.

FIG. 7 is an example timeline 700 demonstrating how the process 600 may be used to adaptively standardize EEG data collected by the plurality of discrete wireless EEG sensors. In the timeline 700, the x-axis illustrates time, and the y-axis illustrates the value of a preprocessing parameter. Based on a detected change, the preprocessing parameter value may be adjusted, as illustrated in FIG. 7 at time 702.

Advantageously, adaptive preprocessing approaches described herein can facilitate an increased freedom of movement (resulting from the use of independent wireless EEG sensors) and increase the duration of an EEG monitoring session during which the EEG sensors are substantially continuously recording EEG data. Rather than being restricted to a hospital bed or specialized observation facility, as is the case with wired EEG monitoring systems, patients may wear the discrete wireless sensors for a period of days or weeks.

In some approaches, EEG data can be adaptively normalized in the feature space, which can obviate the need for adaptive processing. Extracted features can be normalized, such as by performing rolling normalizations or moving normalizations as disclosed herein. Under such approaches, normalization can be adaptive since it is applied to a rolling window of data so that normalization parameters change depending on the characteristics of data.

Adaptive Removal of Noise

In some implementations, preprocessing can include denoising, which in turn can include identification and removal of the noise components from the EEG data. It may be difficult to differentiate the noise in the EEG data from the underlying brain signal due to highly non-static nature of the noise. Denoising techniques that use the statistics of the whole signal or otherwise act by broadly attenuating certain frequencies may fail to distinguish the changes in the statistics of the underlying signal from the intrusion of noise. Advantageously, a denoising approach that adapts to these changing statistics has been developed.

Such approach can remove linear combinations of frequency components that have the worst signal-to-noise ratio (SNR) and then reconstruct the signal from only the components with better SNRs. Advantageously, the developed approach operates on discrete segments of the time series independently, and therefore these components can be selected on a per-segment basis. If the frequency statistics of the underlying signal change, the developed approach can selectively remove different combinations of frequencies.

EEG data may be divided into segments. Segment duration may be between 1 second and 1 hour, such as, 1 second, 2 seconds, 30 seconds, 1 minute, 2 minutes, 5 minutes, 10 minutes, 30 minutes, an hour, etc. EEG data segments may be decomposed into a plurality of frequency components signals using a suitable transform, such as a short Fourier transform and/or a continuous wavelet transform. For a particular segment, the result can be a measure of frequency powers across many frequencies over time (or the duration of the segment). The frequency spectral representation can be transposed and decomposed via principal component analysis (PCA). Principal components (representing linear combinations of frequencies) explaining the least variance can be progressively dropped until only the principal components explaining the most variance are retained. A threshold can be used to drop principal components that do not satisfy the threshold. As a result, the dimensionality of the component representation can be reduced. This reduced representation in component space can be used to reconstruct the frequency power representation via an inverse transform. The reconstruction can be inverse-frequency transformed to reconstruct the time-series segment without the noise components.

In some variations, the number of components used in the principal component analysis reconstruction can be selected based on the minimum description length between the spectral power distribution of the reconstruction and the spectral power distribution of the original EEG segment. Minimum description length minimization may be designed to select the best compression of the data in the sense of a balance between successfully compressing the EEG data (and therefore learning the underlying patterns) and how much EEG data is actually lost in the compression. It may be advantageous to select a number of PCA components representing a good tradeoff between dispensing with the insignificant parts of the EEG signal in the frequency domain (thereby learning the underlying meaningful patterns) and accurately reproducing the original signal's frequency characteristics.

Denosing approaches described in this section can part of the preprocessing block 424 of FIG. 4A. In some instances, denoising approaches described in this section may be used before or after adaptively standardizing EEG data, as described in the previous section. In some implementations, denoising approaches described in this section may be used in place of adaptively standardizing EEG data.

Augmentation of Extracted EEG Data Features

Training a seizure detection pathway (such as, the seizure detection pathway 420 of FIG. 4A) can be challenging particularly when the seizure detection pathway is intended to detect specific electrographic seizure characteristics across a diverse group of patients. In many cases, available training data may include only a limited EEG dataset collected from a small patient population. Disadvantageously, such limited training data may have a bias toward a particular region of the patient's brain. For example, a training dataset may be biased toward seizures that occur on a right side of the patient's brain. Meta-feature creation approaches described herein can generalize the patient EEG data to account for or circumvent any potential biases by generalizing the patient EEG data and increasing the sensitivity of the seizure detection pathway while decreasing the false positive rate. In particular, meta-feature generation can create across-all-sensor features where location is no longer important. As described herein, meta-features can be utilized for training and/or detection of one or more seizure events.

Figure 8:
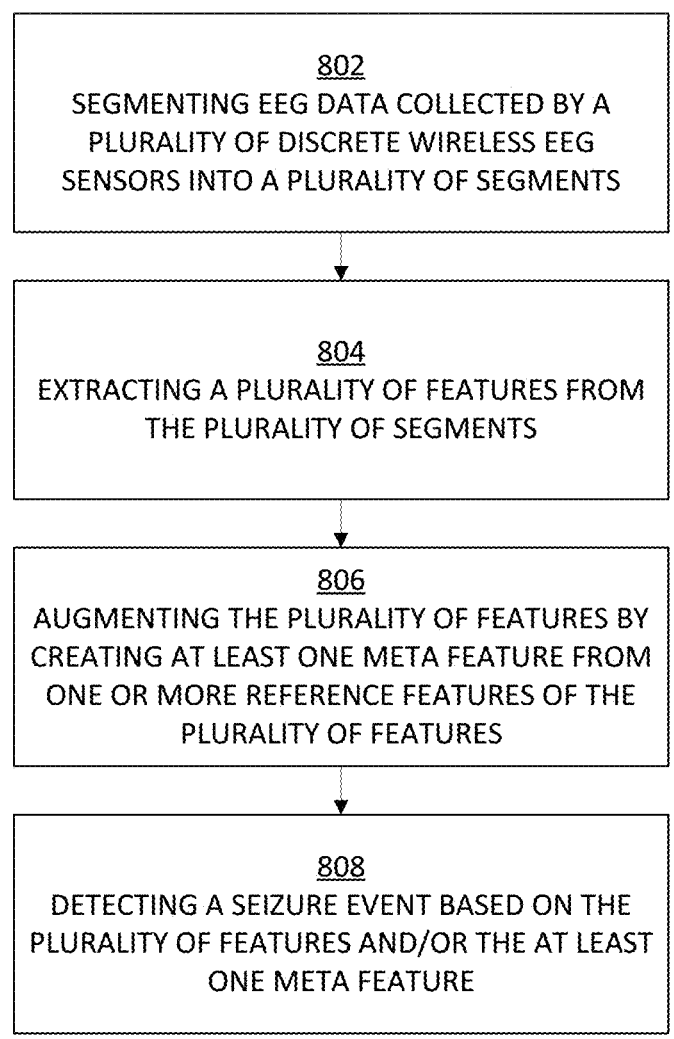
FIG. 8 is an example process for augmenting a plurality of features to create a meta-feature.

FIG. 8 is an example process 800 for augmenting a plurality of features to create a meta-feature. The process 800 can be executed by one or more computing devices, such as by the remote computing device 304 alone or in combination with the one or more portable computing devices 302 or wearable sensors 301. The process 800 may include more or fewer steps. One or more of the steps of process 800 may be performed in a different order or simultaneously with respect to one or more of the other steps of process 800. Instructions for executing the process 800 may be stored on a computer readable medium. The instructions may cause one or more processors to perform the step(s) of the process 800.

The process 800 can be utilized to train a classifier of a single seizure detection pathway (such as, the seizure detection pathway 420 in FIG. 4A) or multiple seizure detection pathways (such as, those described in connection with FIGS. 4B and 5).

The process 800 may begin at step 802 where EEG data channels may be segmented into a plurality of segments. As discussed above, each sensor of a plurality of discrete wireless EEG sensors may be placed on the scalp of a patient and provide an EEG data channel. Each of the plurality of EEG data channels may be segmented into a plurality of EEG data segments. The plurality of data segments may be associated with the originating EEG sensor. For example, a segment generated from an EEG data channel provided by a first discrete wireless EEG sensor may be associated with the first sensor. As discussed above, the plurality of segments may be of a segment length. For example, the plurality of segments may each be 2 seconds.

Step 802 may include one or more aspects of the segmenting step of a single seizure detection pathway, such as, in connection with the block 426 of FIG. 4A or differentiated seizure detection pathways. In some instances, the plurality of EEG channels may be compiled into patient EEG data. The patient EEG data may be segmented into the plurality of EEG segments.

The process 800 may move to step 804 where a plurality of features are extracted from the plurality of EEG data segments. The plurality of features may be extracted to form at least one extracted data feature set. Step 804 may include at least some aspects of the feature extraction step of a seizure detection pathway described above, such as in connection with the block 428 of FIG. 4A.

The process 800 may move to step 806 where the plurality of features may be augmented to create at least one meta-feature. A meta-feature may be created from one or more reference features of the extracted feature dataset. A reference feature may be at least one feature extracted from the plurality of segments. A meta-feature can include data related to one or more extracted features, which may be useful to augment the extracted feature dataset. A meta-feature may generalize data from one or more EEG channels, for example, by pooling the channels, which may reduce artifacts associated with how the data characteristics present differently across the plurality of discrete EEG sensors.

Augmenting the plurality of features may include pooling the one or more reference features to create at least one meta-feature. The meta-feature may be derived from at least one corresponding or related feature associated with at least two EEG data channels (such as, by utilizing pooling, correlation, division etc.) or from a single EEG data channel (such as, by utilizing trends, moving averages, moving normalization, etc.). For example, when discrete EEG sensors are utilized, pooling can provide a feature that is derived from a subset of (or all) EEG channels associated with the discrete EEG sensors. For instance, pooling can include taking a maximum (or minimum, averaged, etc.) value across all EEG channels, which may allow for generalization of a seizure event regardless of the origination and/or sensor ordering. Advantageously, pooling can allow the classifier to become agnostic to the order of the EEG channels and/or location and, consequently, become more robust even when trained with a smaller set of EEG data and, in use, for detection of seizure events.

For example, suppose that feature A (FA) for four EEG channels has been determined as FA_1, FA_2, FA_3, and FA_4. Each of these can be independent features that may be independently used by a classifier of the seizure detection pathway. A pooing meta-feature can be the minimum, maximum, mean, variance, etc. of the four features FA_1, FA_2, FA_3, and FA_4. Let's assume that FA_1=1, FA_2=1, FA_3=2, and FA_4=7. The minimum pooled meta-feature would be 1. The maximum pooled meta-feature would be 7. The mean pooled meta-feature would be 2.75. One or more (or all) of such pooled meta-features can be utilized during the classification. In some instances, one or more meta-features along with one or more features may be utilized for seizure event detection (such as, in step 808). In some cases, only the meta-feature(s) may be utilized and feature(s) may be dropped in order to make the detection fully generalized.

One or more meta-features can be derived from any of the time domain, frequency domain, or complexity domain features. Meta-features can allow the classifier to be location agnostic. For instance, a meta-feature that corresponds to the mean of entropy would serve such purpose. In some instances, meta-features can allow the classifier to hone in on the location in time of a possible seizure event. For example, a meta-feature that corresponds to the variance of band power, which would indicate the differences across the four EEG channels, would serve such purpose.

Meta-features can be derived to serve as cross-channel generalizers (such meta-features would be location agnostic). Meta-features can be derived to determine cross-channel statistics. Meta-features can be derived to be per-channel over-time generalizers (for instance, running average of a feature).

Meta-features may be determined using first order (such as, differential of a feature or variance of a feature), second order (such as, variance of the differential of a feature), or the like statistical analyses. In some cases, compound meta-features can be determined (such as, a running average of a pooled feature). For example, a relative band power feature for each EEG data channel may be determined and averaged to create a pooled relative band power feature. An extracted feature may be pooled temporally such as, across a segment window that includes a plurality of segments for one or more EEG data channels to create the at least one meta-feature. For example, a mean differential voltage value may be pooled temporally across a segment window to generate a running average meta-feature. As yet another example, a meta-feature may be created based on a moment-to-moment variance of extracted feature(s). The moment-to-moment variance may be determined based on the variance of the extracted feature(s) across a time period (such as, seconds, minutes, or hours in length). As yet another example, a meta-feature can be created based on long-term temporal analysis of the extracted feature(s), which may be conducted over a period of minutes, hours, days, weeks, etc. to identify trend(s). The long-term temporal analysis may include computing running averages, variances, etc. The long-term temporal analysis may associate EEG data based on a time of day and/or patient activity level. For example, the long-term temporal analysis may determine a running average and/or average variance of EEG data for a patient at bedtime.

Meta-features can be created from one or more features extracted from a single EEG data channel (such as, differential, variance, maximum, minimum, etc.) or from one or more features extracted from multiple EEG data channels (such as, cross-channel variance, cross-channel maximum, cross-channel minimum, etc.).

The process 800 may move to step 808 where a seizure event is detected based on the extracted feature dataset and/or the at least one meta-feature. Step 808 may include aspects of the classification and event identification steps described above in conjunction with FIG. 4A (such as, the blocks 430, 432, and 434 of FIG. 4A). Similar to the block 430 of FIG. 4A, step 808 may include applying a classifier that identify a seizure event within a segment of the plurality of segments. The classifier may make this determination based on the extracted EEG data features and/or the at least one meta-feature.

As described herein, the process 800 may include training a classifier of a seizure detection pathway using the at least one meta-feature. As described above, the one or more models may be differentiated among a plurality of seizure detection pathways configured to detect a plurality of differentiated electrographic seizure characteristics.

In some cases, the creation of one or more meta-features may be differentiated for differentiated seizure detection pathways. For example, a first seizure detection pathway can create and utilize a first set of meta-features and a second seizure detection pathway can create and utilize a second set of meta-features different from the first set of meta-features. As another example, a first seizure detection pathway can create and utilize a first set of meta-features and a second seizure detection pathway may not create any meta-features.

Figure 9:
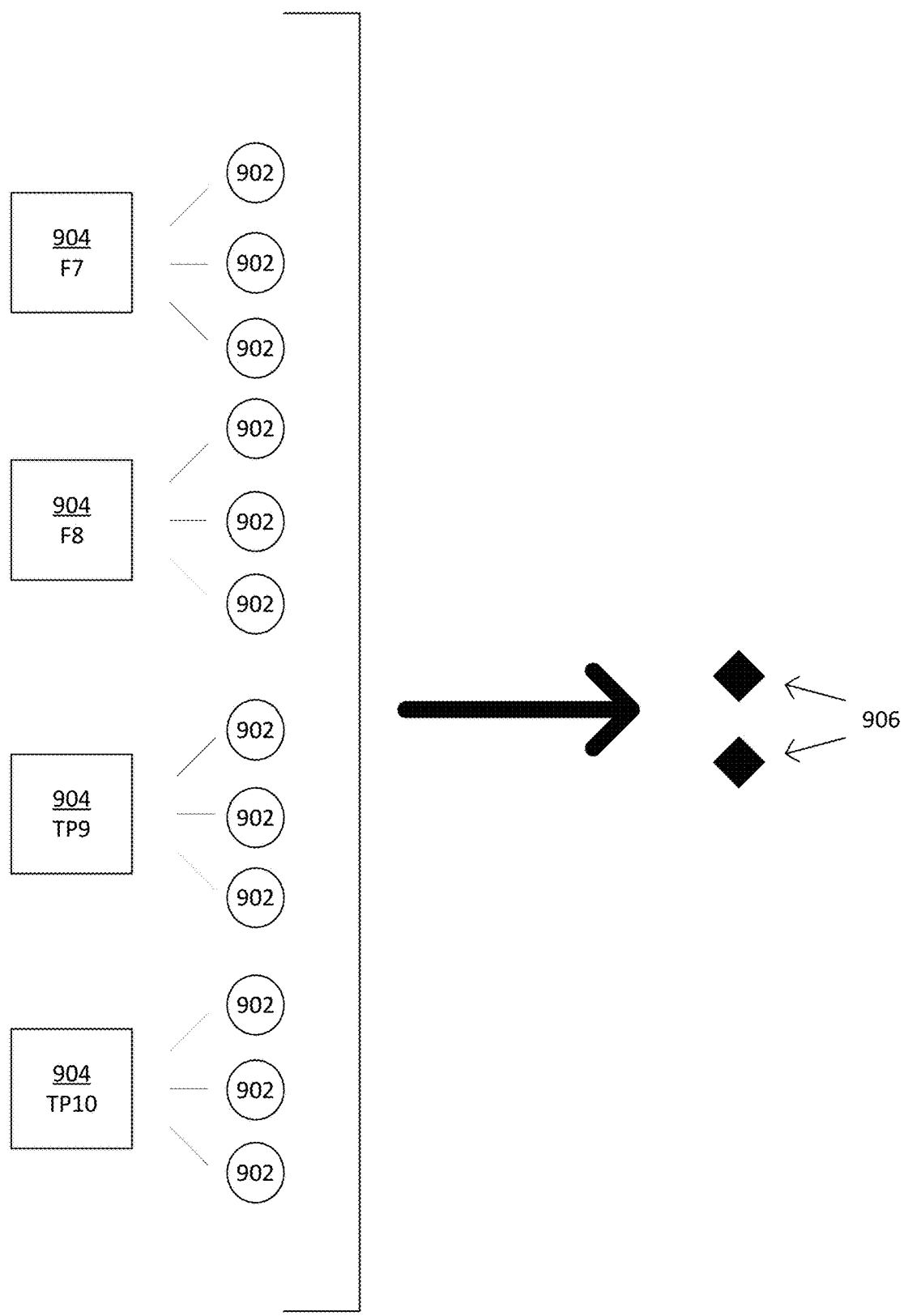
FIG. 9 illustrates how a plurality of features may be extracted and augmented to create one or more meta-features.

FIG. 9 illustrates how a plurality of features 902 may be extracted from a plurality of EEG data channels 904 and augmented to create one or more meta-features 906. The plurality of EEG data channels 904 may be collected by four discrete EEG sensors placed on the scalp of a patient at four discrete locations. For instance, the locations can correspond to the left and right frontal (noted as F7 and F8, respectively) and temporoparietal areas (noted as TP9 and TP10, respectively).

Augmentation of EEG Data for Training

Training a seizure detection pathway (such as, with the seizure detection pathway 420 of FIG. 4A) can be challenging particularly when the seizure detection pathway is intended to detect specific electrographic seizure characteristics across a diverse group of patients. Ideally, very large sets of training data that reflect many different data capture scenarios for the diverse group of patients would be used to train the seizure detection pathway. Obtaining such sets of training data may not be feasible. Instead, smaller sets of training data can be extended to cover various data capture scenarios and create training datasets of sufficient variety to train the seizure detection pathway to operate with a target sensitivity and false positive rate. In addition, extending smaller sets of training data can be particularly important in case when the training data has been obtained with a small number of EEG sensors attached to the scalp, such as four discrete wireless sensors as described herein. EEG data channels obtained from such sensor arrangements can be extended to create training datasets that include additional features. Advantageously, this can improve convergence of a classifier of the seizure detection pathway and improve robustness of the pathway.

Training data can be extended by scaling, flipping (or scaling by −1), adding noise, permuting, changing an associated position, or the like of one or more EEG data channels of a training dataset. For example, an EEG data channel produced by a particular EEG sensor can be multiplied by −1 to mimic positioning the particular EEG sensor in a reverse orientation on the patient's scalp. As another example, EEG data collected by an EEG sensor positioned at the left forehead can be swapped with EEG data collected by an EEG sensor positioned at the right forehead, which is an example of permuting. As a result, the training set can include a first set of EEG data with data collected by the sensors positioned at the left and right forehead and a second set of EEG data with the EEG data from the swap. This way, the training set can be extended to make a classifier of the seizure detection pathway more robust and more agnostic to the location of the possible seizure event. As yet another example, EEG data collected by an EEG sensor positioned behind the left ear can be swapped with EEG data collected by an EEG sensor positioned behind the right ear, which is another example of permuting. This way, the EEG dataset can be extended and used for training the classifier of a seizure detection pathway.

As yet another example, different expected noise characteristics that may be present in the real-world, such as 60 Hz line noise, mechanical noise (such as, from a hairdryer), or electromagnetic noise emitted by a microwave, can be added to the EEG data. Adding such noise characteristics to the raw EEG data can not only extend the training data, but also create more diverse real-world simulations that can make the classifier more robust.

Figure 10:
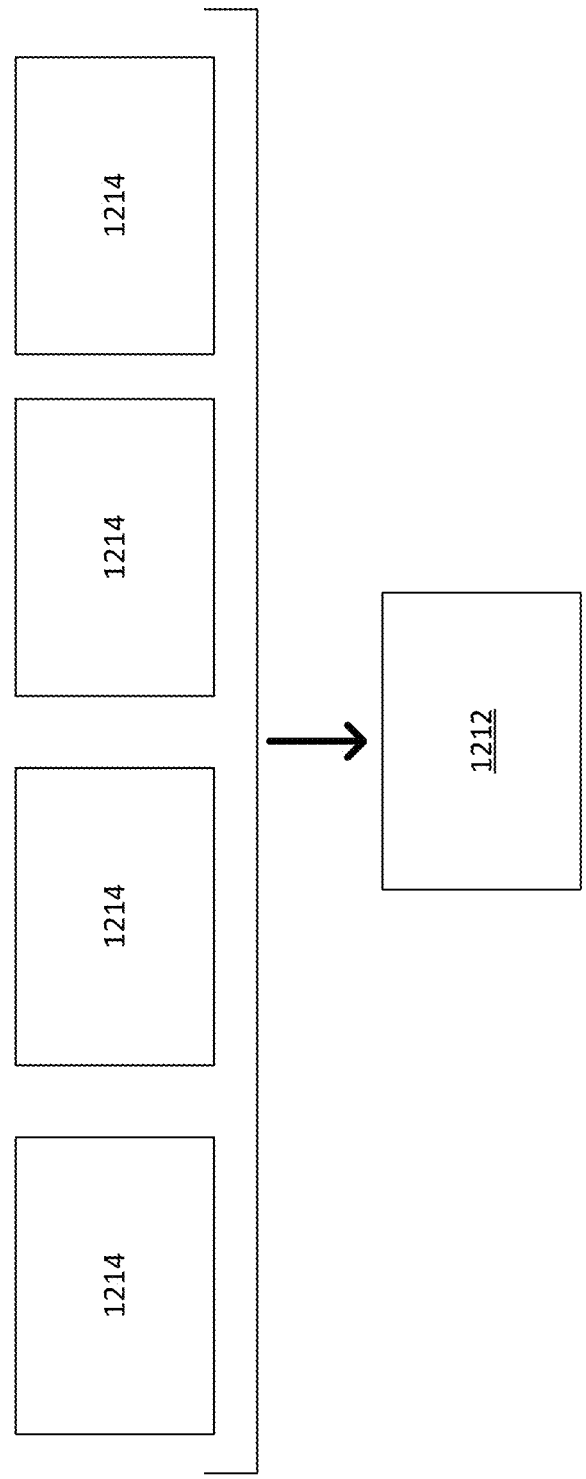
FIG. 10 illustrates an example of augmenting EEG data for training.

FIG. 10 illustrates creating a new EEG data channel 1212 based on a plurality of EEG data channels 1214. The new EEG data channel 1212 and the plurality of EEG data channels can utilized for training. One or more seizure detection pathways may be trained to detect seizure events using the plurality of EEG data channels and the new EEG data channel. A particular seizure detection pathway may be trained to detect differentiated electrographic seizure characteristics. As described herein (such as, in connection with FIGS. 4A-4B and 5), the seizure detection pathway may include a classifier that is trained to detect seizure events using the plurality of EEG data channels 1214 and the new EEG data channel 1212 (or multiple such EEG data channels).

Identifying Seizure Events

As described herein, seizure detection can be performed on EEG data segments of a particular duration. A seizure event can include multiple segments. Some seizure detection approaches rely on comparing the detected seizure probabilities for the segments to a threshold. If a probability for a given segment satisfies the threshold, the segment is determined to be part of a seizure event. A discrete seizure event would then be determined as starting when the first data segment goes above the threshold and ending when the first data-segment goes below the threshold. Such approaches are susceptible to errors when encountering an errant segment with an errant probability. The errant segment can be incorrectly interpreted as an end (or beginning) of a discrete seizure event.

Advantageously, event identification approaches described herein can effectively solve at least these technical problems related to the detection of seizure events, such as discrete seizure events. Unlike previous seizure detection approaches, using different event identifiers within a seizure detection pathway and across different seizure detection pathways can achieve a target sensitivity and false positive rates across diverging patient populations. As described herein, in some instances, at least 70% sensitivity and a false positive rate of no more than about 0.21 false positives per hour (o no more than 0.08 false positives per hour) can be achieved.

Figure 11:
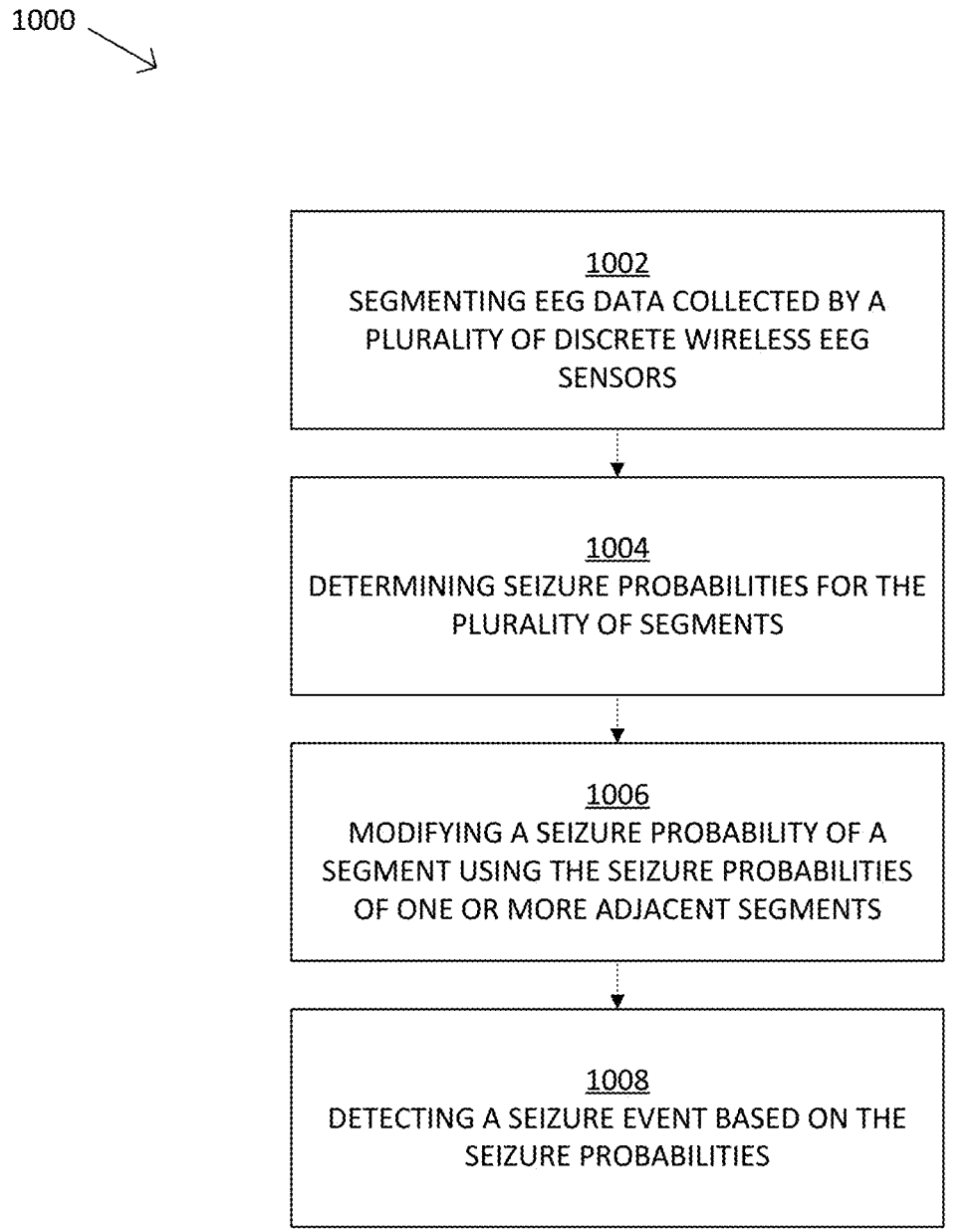
FIG. 11 is an example process for detecting seizure events.

FIG. 11 is an example process 1000 for detecting seizure events. The process 1000 can be executed by one or more computing devices, such as by the remote computing device 304 alone or in combination with the one or more portable computing devices 302 or wearable sensors 301. The process 1000 may include more or fewer steps. One or more of the steps of process 1000 may be performed in a different order or simultaneously with respect to one or more of the other steps of process 1000. Instructions for executing the process 1000 may be stored on a computer readable medium. The instructions may cause one or more processors to perform the step(s) of the process 1000.

The process 1000 may begin at step 1002 where patient EEG data may be segmented into a plurality of segments (for instance, as described in connection with the block 426 of FIG. 4A). As discussed above, each sensor of a plurality of discrete wireless EEG sensors may be placed on the scalp of a patient and provide an EEG data channel. The plurality of EEG data channels may be compiled as patient EEG data and segmented into a plurality of segments of a segment length. For example, the plurality of segments may each be 2 seconds long. Each of the plurality of EEG data channels may be segmented independently. Step 1002 may include one or more aspects of the segmenting step of the differentiated seizure pathways discussed above (such as, described in connection with FIGS. 4B and 5). In some implementations, a segmenting step of a plurality of seizure detection pathways may be differentiated, as described above.

The process 1000 may move to step 1004 where a probability that a seizure activity has been identified by a classifier (sometimes referred to as seizure probability) may be determined for each segment of the plurality of segments. Step 1004 may include some or all of the aspects of the classification step of a seizure detection pathway described above in conjunction with FIGS. 4A-4B and 5. In some instances, a classifier may be applied to determine the probability of a seizure event within the segment based on the at least one feature extracted from the segment. The probability value may be determined on a scale, which may range from 0 to 1.

The process 1000 may move to step 1006 where the probability determined for a segment is modified based on the probabilities determined for one or more adjacent segments. Step 1006 may include some aspects of the event identification step (or stitching) described above in conjunction with the differentiated seizure detection pathways (such as, in connection with FIGS. 4B and 5). Step 1006 may include applying one or more event identifiers to analyze the determined probabilities for the one or more segments (such as, for one or more segments in a segment window). In some instances, an event identifier may assess, for a particular segment, the probability value for the segment and one or more probability values of one or more adjacent segments.

In some implementations, one or more of filtering, smoothing, thresholding, and morphological transformation processes are used to convert segment probabilities into seizure events (such as, discrete seizure events) to satisfy target sensitivity and false positive rate.

To address the problem of errant segments and probabilities, an event identifier may modify the probability value for the segment using one or more morphological transformations. In some instances, one or more morphological transformations may operate to binary probability values (such as, 0 and 1 rather than on continuous values in the range between 0 and 1). The probability value for a segment may be converted to a binary probability value based on a probability threshold. For example, if the probability value is less than the probability threshold, a binary value of 0 may be assigned to the segment (which may, at least initially, indicate that no seizure has been identified). Conversely, if the probability value is greater than the probability threshold, a binary value of 1 may be assigned to the segment (which may, at least initially, indicate that a seizure has been identified). In some implementations, the probability threshold may be differentiated between seizure detection pathways. For example, the event identification step of differentiated seizure detection pathways may be differentiated by applying different probability thresholds.

The binary value of a particular segment may be modified based on the binary value of one or more adjacent segments using one or more morphological transformations, which may include modifying the probability value of a segment based on the probability values of one or more adjacent segments. For example, the probability value of the segment that does not exceed the probability threshold may be adjusted to exceed the threshold based on the probability values of one or more adjacent segments exceed the probability threshold. The probability value of the segment that exceeds the probability threshold may be adjusted to not exceed the threshold based on the probability values of one or more adjacent segments not exceeding the probability threshold.

One or more morphological transformations can include erosion, dilation, opening (or erosion followed by dilation), and closure (or dilation followed by erosion). In some implementations, one or more morphological transformations performed by an event identifier may include one or more of the following operations: 1) "removal" of gaps (continuous segments with binary value of 0 between continuous segments with binary value of 1) that are shorter than a minimum gap threshold (such as, 2, 3, 4, etc. consecutive segments depending on the segment length), 2) "removal" of segments with binary of value of 1 having duration that is less than a minimum discrete seizure duration threshold (such as, 2, 3, 4, etc. consecutive segments depending on the segment length), and 3) padding of discrete seizure events by particular padding factor (such as, 10, 20, 30, etc. depending on the segment length). Because morphological operation #1 may be associated with dilation is followed by a morphological operation #2 that may be associated with erosion, the sequence of these morphological operations can be associated with a morphological closure.

Removal may be accomplished by modifying the binary value of one or more affected segments (such as, modifying the binary value from 0 to 1 or vice versa). For example, suppose that two consecutive "no seizure" segments with binary values of 0 may be flanked by continuous "seizure" segments with binary values of 1. Also, suppose that the minimum gap threshold is 3. In accordance with the morphological transformation operation #1, which may be associated with dilation, the binary value of the two adjacent "no seizure segments" would be modified to 1 to remove the gap associated with a spurious no seizure event. As another example, suppose that there are two consecutive "seizure" segments are flanked by "no seizure" segments, and that the minimum discrete seizure duration threshold is 3. In accordance with the morphological transformation operation #2, which may be associated with erosion, the binary value of the two adjacent "seizure" segment would be modified to 0 to remove the spurious seizure event.

As an example of padding associated with the morphological transformation operation #3, which may associated with dilation, a discrete seizure event may be extended to capture one or more adjacent segments with binary values of 0. This may facilitate clinician's review of the EEG data. In some instances, the padding operation can be omitted. The padding operation may be differentiated among a plurality of seizure detection pathways. For example, an absence seizure may last for at least about 10 seconds, while a focal seizure may last for a minimum duration of about 2 minutes. Accordingly, one or more event identifiers for a seizure detection pathway designed and tuned to detect one or more electrographic seizure characteristics that may be related to absence seizures may pad to ensure a minimum duration of about 10-15 seconds. One or more event identifiers for a seizure detection pathway designed and tuned to detect one or more electrographic seizure characteristics that may be related to focal seizures may pad to ensure a minimum duration of about 1-2 minutes.

In some instances, the probability value for a segment may be modified based on a moving average and/or a variation of the probability values of the one or more segments. This type of smoothing can be performed prior to the one or more morphological transformations.

The process 1000 may move to step 1008 where a whole seizure event may be detected. The whole seizure event may span the segment whose probability value was modified and the one or more adjacent segments. A start time and a stop time and/or duration as well as a confidence value of the whole seizure event may be determined.

Using the approaches described herein, seizure events (such as, whole seizure events) may be detected with a target sensitivity and a false positive rate. The sensitivity and false positive rates may be inversely correlated but tuned to meet output standards. In some implementations, whole seizure events may be detected with a sensitivity between about 70% to about 90% (such as, at least 80%) and a false positive rate of about 0.21 false positives per hour (or, in some cases, of about 0.08 false positives per hour).

Channel Augmentation

EEG data collected by a sensor of a plurality of sensors may be lost as a result of one or more malfunctions. For instance, when discrete wireless EEG sensors are used (such as, sensors 101 or 301), EEG data collected by one or more of the sensors can be lost, for instance, in transmission. The approaches described herein advantageously can address these problems by generating a missing EEG data channel (or missing data channels) from received EEG data channels. Training and/or seizure detection may be performed using the received EEG data channels along with the generated EEG data channel.

Figure 12:
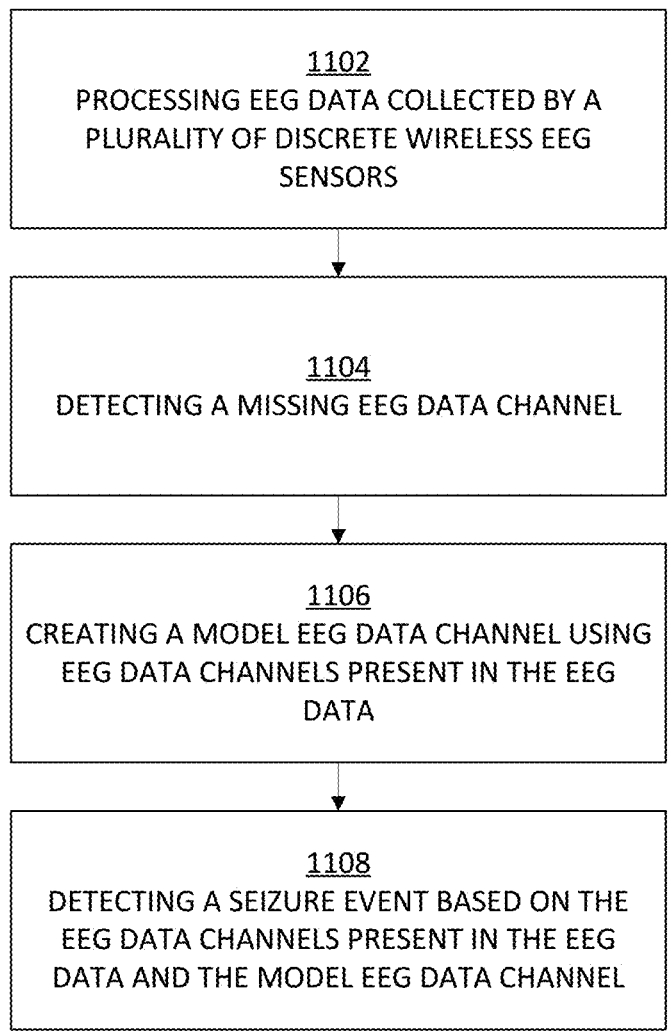
FIG. 12 illustrates modifying a probability of a segment of EEG data using the probability of one or more adjacent EEG data segments.

FIG. 12 is an example process 1100 for creating a model (or synthetic) EEG data channel, which may be used in place of the missing EEG data channel. The process 1100 can be executed by one or more computing devices, such as by the remote computing device 304 alone or in combination with the one or more portable computing devices 302 or wearable sensors 301. The process 1100 may include more or fewer steps. One or more of the steps of process 1100 may be performed in a different order or simultaneously with respect to one or more of the other steps of process 1100. Instructions for executing the process 1100 may be stored on a computer readable medium. The instructions may cause one or more processors to perform the step(s) of the process 1100.

The process 1100 may begin at step 1102 where EEG data collected by a plurality of discrete wireless EEG sensors disposed on the scalp of a patient is processed. The EEG data collected by the plurality of discrete wireless EEG sensors may be processed using one or more seizure detection pathways, as described herein in connection with FIGS. 4A-4B and 5. In some instances, one or more seizure detection pathways may be configured to detect differentiated electrographic seizure characteristics from the EEG data collected by the plurality of discrete wireless EEG sensors.

As described herein, the plurality of discrete wireless EEG sensors may include four EEG sensors placed on a scalp of the patient at locations corresponding to the left and right frontal and temporoparietal areas. For example, the four EEG sensors can be placed at a left forehead location corresponding with an F7 location, a right forehead location corresponding with an F8 location, a location behind the left ear corresponding with a TP9 location, and a location behind the right ear corresponding with a TP10 location.

Each discrete wireless EEG sensor may provide an EEG data channel. The EEG data channel may be associated with a location of the corresponding EEG sensor. For example, the EEG data channel may be associated with the precise location of the discrete wireless sensor, such as an F7 location or a TP10 location. In some cases, the EEG data channel may be associated with a cerebral hemisphere of the patient. For example, the EEG data channel may be associated with the left hemisphere or the right hemisphere, which may be defined in relation to the medial plane of the patient. In another example, the EEG data channel may be associated with the anterior hemisphere or the posterior hemisphere, which may be defined in relation to the frontal plane of the patient. In some instances, the EEG data channel may be associated with a lobe of the patient's brain such as the frontal lobe, the parietal lobe, the occipital lobe, or the temporal lobe based on the lobe closest to the location of the corresponding EEG sensor.

Next, the process may move to step 1104 where a missing EEG data channel may be detected. The number of EEG data channels provided or received from the EEG sensors may be compared to an expected number of EEG data channels. If the number of EEG data channels is less than the number of expected channels, a missing EEG data channel may be detected. For example, as discussed herein, the EEG data channels may be independently transmitted to a portable computing device (such as, the device 302) by the plurality of discrete wireless EEG sensors and compiled into patient EEG data. The portable computing device may receive 3 EEG data channels when 4 EEG data channels are expected, and thus a missing EEG data channel may be detected.

In some implementations, the missing EEG data channel may be detected based on the locations associated with the EEG data channels. Continuing with the above example of the four discrete wireless EEG sensors, a portable computing device (or another computing device) may expect to receive an F7 EEG data channel, an F8 EEG data channel, a TP9 EEG data channel, and a TP10 EEG data channel. However, only the F8 EEG data channel, the TP9 EEG data channel, and the TP10 EEG data channel may be received. Accordingly, the portable computing device may detect that the F7 EEG data channel is missing. The EEG data channel may be missing due to a failure of a discrete wireless EEG sensor.

The process 1100 may move to step 1106 where a model EEG data channel is created. The model EEG data channel may be created based on the EEG data channels present in received the EEG data. The model EEG data channel may be created based on EEG data collected from a patient population. As discussed herein, the patient population may include a patient, a group of patients who suffer from a particular seizure type, a group of patients who suffer from any type of seizure, or a group of patients that includes a first subgroup of patients who suffer from seizures and a second subgroup of patients that does not suffer from seizures. The model EEG data channel may be created based on the EEG data channels present in the EEG data and EEG data collected from a patient population.

A model EEG data channel may be created using (such as, modifying) one or more present EEG data channels based on the location of the missing EEG data channel and the location of the present EEG data channel(s). For example, the location of the missing EEG data channel may be on the opposite side of the median plane from at least one EEG data channel. The model EEG data channel may be created by modifying the at least one EEG data channel. As an example, an EEG data channel obtained from an EEG sensor positioned behind the left ear may be used to generate the model EEG channel corresponding to location behind the right ear (for instance, using shadow manifold cross sampling as described herein). In another example, the location of the missing EEG data channel may be associated with a first EEG sensor positioned on the opposite side of the frontal plane from a second EEG sensor that has provided at least one EEG data channel. The model EEG data channel may be created by modifying the at least one EEG data channel (for instance, using shadow manifold cross sampling as described herein).

A model EEG data channel may be created through shadow manifold cross sampling (SMaCS). Shadow manifold cross sampling (SMaCS) is a technique for generating highly realistic, synthetic EEG data that can share many important statistics with real EEG data and can be used to replace missing EEG channel(s) or augment existing data to expand the training sets. SMaCS may use an existing EEG data channel as a base signal and emulate that signal by forcing a stochastic differential equation that is derived from the statistics of the original signal's sample-wise differentials to maintain similar longer-term temporal relationships to those found in the base signal. The base signal can be selected as an EEG data channel that is contralateral to a missing EEG data channel, as described herein. The output of SMaCS can be used to replace the missing EEG data channel with data from the contralateral EEG data channel or to augment EEG datasets with all EEG data channels by selectively replacing channels with an SMaCS synthetic time series derived from the contralateral channel to expand training sets. SMaCS is a general-purpose method of generating synthetic EEG data and can be used in any cases that would require or benefit from such data. SMaCS can be used during training and seizure detection.

SMaCS can include two parts as follows. The first part can be related to stochastic process sampling and emulation. A base EEG signal S can be treated as a stochastic process and probability density function estimates (P) of the original signal's sample-wise differentials (hereafter referred to as first-order differentials) can be gathered for intervals over the output range of S. This can produce mapping of any given EEG data channel sample at time t (St), to a probability distribution of first-order differentials given the specific value range of St. The range of signal S can be divided into M non-overlapping bins covering the range. The bins may or may not be equally sized. A set P of probability density estimates of the values of S belonging to each interval R (corresponding to the M bins) can be created. Any given $P_{Rk}$ can represent a probability density estimate of the derivatives of S in the range $R_k$.

A mapping function G between values in the range of S and the probability density estimates for values in the appropriate intervals R can be defined ($G=x\in R_k \rightarrow P_{Rk}\in P$). Thus, given some value on S's range, G produces a probability density function P. Sampling P's provided by G allows generation of a stochastic process by integrating a function using the sampled values as derivatives. This stochastic process models the original EEG signal's first-order differential statistics, emulating its moment-to-moment stochastic behavior. A random variable associated with such a stochastic process can be used as part of a model EEG data channel. The second part of SMaCS can include transforming S' such that it behaves as if it were derived from the same dynamical system as S, by transforming its time-delay embedding to have a similar structure to that of S (for instance, as per Takens' theorem). The final result can be a temporal structure cross-sampling or the projection from EEG signal's(S) shadow-manifold onto the random signal generated by the random process, thus generating the model EEG data channel.

Next, the process 1100 may move to step 1108 where a seizure event may be detected based on the EEG data channels present in the EEG data and the model EEG data channel. Step 1108 may include processing the present EEG data channel(s) and the model EEG data channel with one or more seizure detection pathways. For example as described herein (such as, in connection with FIGS. 4A-4B and 5), the present EEG data channels and the model EEG data channel may be preprocessed and segmented into a plurality of segments, a plurality of features may be extracted from the plurality of segments, and a seizure event may be detected by applying a classifier based on the plurality of features.

Figure 13:
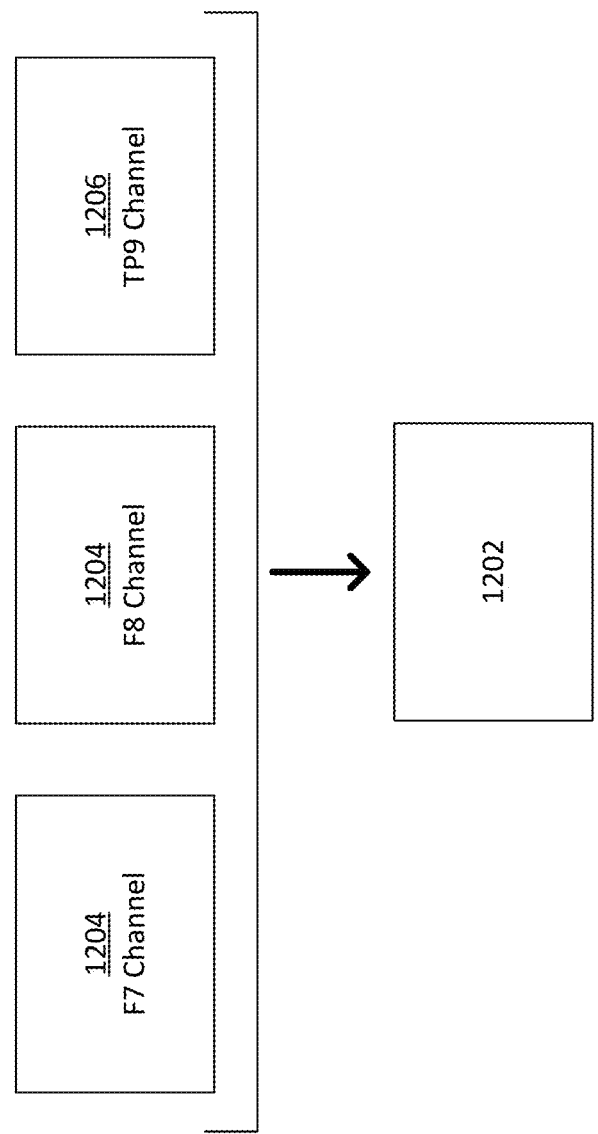
FIG. 13 illustrates an example of recreating a missing EEG data channel.

FIG. 13 illustrates creating a model EEG data channel 1202 based on a plurality of EEG data channels present in EEG data, such as an F7 EEG data channel 1204, an F8 EEG data channel 1204, and a TP9 EEG data channel 1206.

Event Identification and Confidence

As described herein (such as, in connection with FIGS. 4A, 4B, and 5), a seizure detection pathway can be designed and trained for detection of a seizure event. In some implementations, the seizure detection pathway includes multiple event identifiers. As described herein (such as, in the section titled "Seizure Detection Pathway for EEG Data Collection and Processing"), an event identifier can be configured to evaluate EEG data segment probabilities (e.g., 0-1) determined by a classifier of a seizure detection pathway to output a label representing the presence of a temporally extended seizure phenomena (such as, a start time and stop time and/or duration for a discrete seizure event). Some event identifier parameterizations or interpretations of the probabilities may detect more true events at the expense of making more mistakes, while others may detect fewer true events while making fewer mistakes. Thus, a subset of event identifiers that offer beneficial tradeoffs between detecting events and making mistakes can be selected during training, as described herein. A confidence value can be derived from which event identifiers do and do not detect an event in the segment probability data. Event identifier parameterizations that make many mistakes can be less certain in the positive detections, therefore leading to a lesser confidence when they predict an event. On the other hand, event identifier parameterizations that have fewer false detections can be more certain in the positive detections they make, therefore leading to a greater confidence when they predict an event.

Many different parameterizations of an event identification pipeline can be created. It can be determined how frequently they detect true events and how frequently they raise false positives. Among all those tested during training, a subset that provides beneficial tradeoffs between those two measures can be selected for interpreting EEG data collected from a patient. In use on a patient, it may be possible to derive a confidence based on which one or more event identification parameterizations of that subset of event identifier parameterizations detect an event and how frequently such one or more event identification parameterizations made false detections on the training data.

Figure 14:
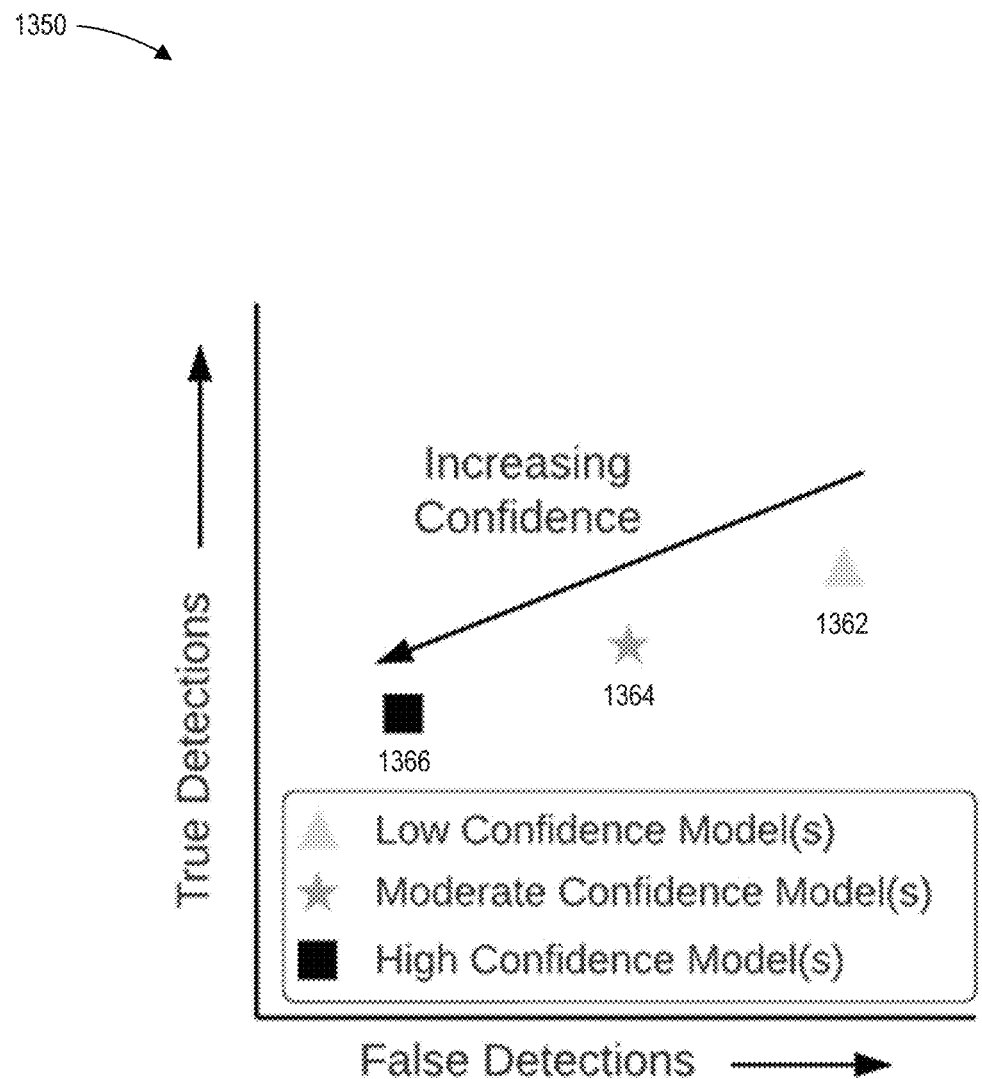
FIG. 14 illustrates confidence levels of various event identifiers.

FIG. 14 shows a plot 1350 with event identifier parameterizations 1362, 1364, and 1366. The x-axis of the plot 1350 corresponds to false detections, and the y-axis corresponds to true detections. Event identifier parameterization 1362 detects more true events but with many mistakes, and can be considered to have a low confidence but with high true detections. Event identifier parametrization 1364 detects less true events with fewer mistakes than 1362, and can be considered to have a moderate confidence. Event identifier parametrization 1366 detects even fewer true events but with very few mistakes than 1362 and 1364, and can be considered to have a high confidence.

When an event is detected by multiple event identifier parametrizations, a confidence value for the event can be determined based on the confidence of the "most" confident event identifier parametrization that has detected the event. For example, if the event identifier parametrization 1362 is the only parametrization that has detected an event, a low confidence value would be assigned to the event. As another example, if the event identifier parametrization 1364 has detected an event (along with likely the event identifier parametrization 1362), a moderate confidence value would be assigned to the event. In yet another example, if the event identifier parametrization 1366 has detected an event (along with likely the event identifier parametrizations 1362 and/or 1364), a high confidence value would be assigned to the event. That is, a confidence value for an event can be assigned based on determining the highest confidence event identifier parametrization has detected the event regardless of any other lower confidence event identifier parametrization that have also detected the event. One or more events detected by event identifier parametrizations having lower confidence can be discarded.

In some instances, a confidence value can be indicative of precision and may be determined as follows:

Confidence = 1 − False Discovery Rate =

1 − False Positives/(True Positives + False Positives)

Figure 15:
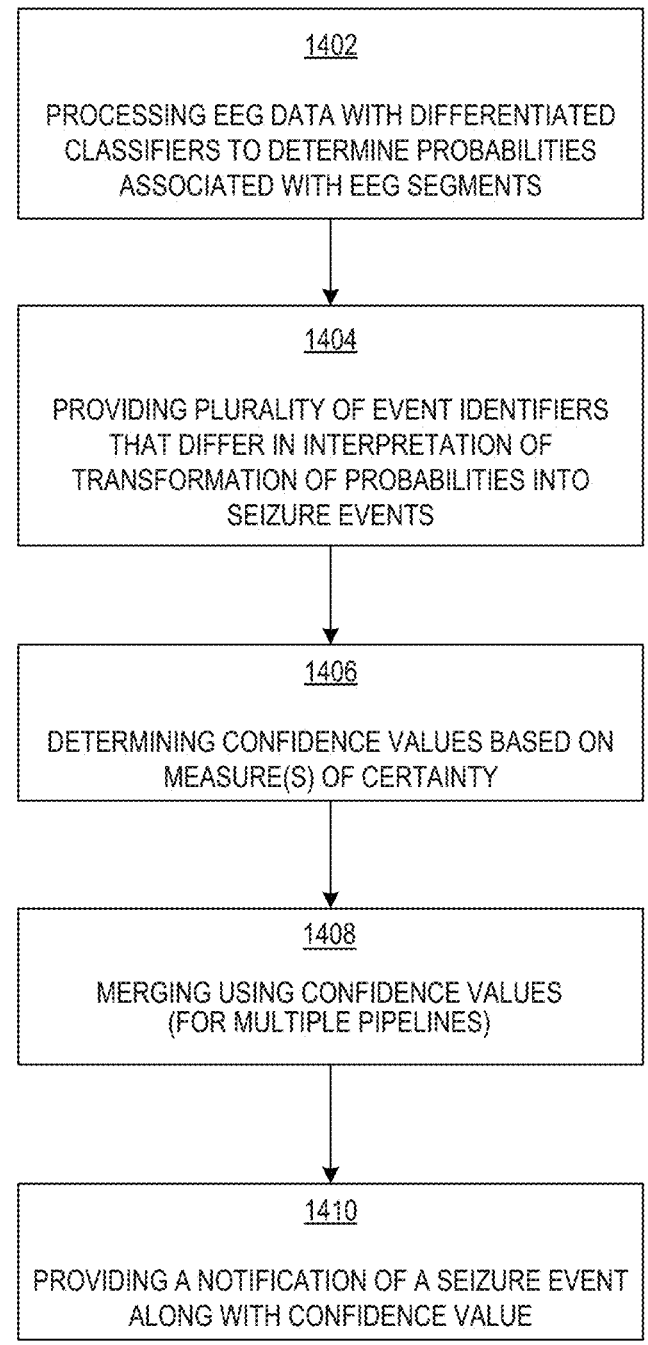
FIG. 15 illustrates an example process for outputting a seizure event along with a confidence level.

FIG. 15 is an example process 1400 for outputting a seizure event along with a confidence level. The process 1400 can be executed by one or more computing devices, such as by the remote computing device 304 alone or in combination with the one or more portable computing devices 302 or wearable sensors 301. The process 1400 may include more or fewer steps. One or more of the steps of process 1400 may be performed in a different order or simultaneously with respect to one or more of the other steps of process 1400. Instructions for executing the process 1400 may be stored on a computer readable medium. The instructions may cause one or more processors to perform the step(s) of the process 1400.

The process 1400 may begin at step 1402 where EEG data collected by a plurality of discrete wireless EEG sensors is processed with a seizure detection pathway (such as, that illustrated in FIG. 4A) and/or a plurality of classifiers of differentiated pipelines (such as, those illustrated in FIG. 4B). The output of step 1402 can be probability values associated with EEG data segments.

The process 1400 can transition to step 1404 where subsets of event identifier parameterizations selected during training transform the probability values into seizure events.

The process 1400 can transition to step 1406 where confidence values are determined based on which one or more event identification parameterizations of a subset of event identifier parameterizations detect an event and how frequently such one or more event identification parameterizations made false detections on the training data.

The process 1400 can transition to an optional step 1408 where seizure events and confidence values output by event identifier parameterizations associated with differentiated pipelines are merged when multiple pipelines are being used. This can be similar to the event merge block 460 of FIG. 4B. As described herein, step 1408 can analyze confidence values of the seizure events determined by the respective event identifier parameterizations. For example, for ex post facto detection, a discrete seizure event associated with the highest confidence value of all detected events may be chosen in step 1408. As another example, for rapid detection, an event that indicates prevalence of an EEG characteristic or pattern that satisfies a prevalence threshold and has the highest confidence may be chosen in step 1408. If there is no event identifier parameterization that outputs an event with such prevalence, an event with the highest confidence may be chosen in step 1408.

Figure 16:
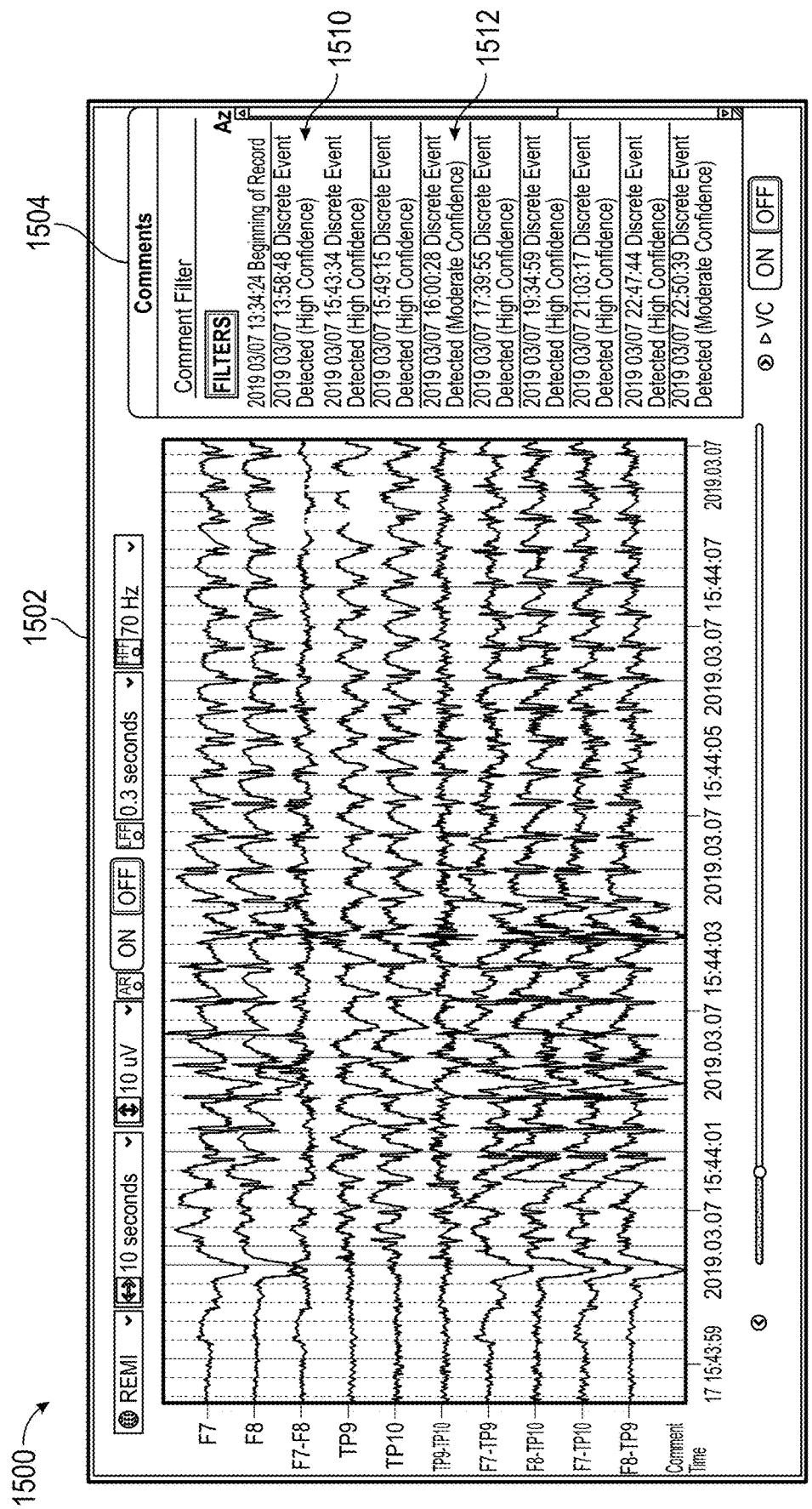
FIG. 16 illustrates seizure event output with confidence values.

The process 1400 can transition to step 1410 where notification of a seizure event along with the confidence value can be provided (see, for example, FIG. 16). Confidence value can be reported as a number (such as, 68%) or a level. The latter may be a more useful tool for a clinician. For example, as described in this section, the confidence level may include 3 possible levels or ratings: a high, a moderate, and low. As another example, the confidence level may include 4 possible levels or ranges: extremely high, high, moderate, and low. In some cases, low confidence can correspond to less than 50%, moderate confidence can correspond to 50% to 79%, high confidence can correspond to 80% to 94%, and very high confidence can correspond to 95% or more. More generally, low confidence can correspond to less than A %, moderate confidence can correspond to A % to B % (where B is greater than A), high confidence can correspond to C % to D % (where C is greater than B but less than D), and very high confidence can correspond to E % (where E is greater than D).

The notification may include a visual, audio, or haptic output. For example, a notification may be generated on a portable computing device. The notification may include an element in a graphical user interface that includes an indication of the possible seizure and the confidence level. The indication may include information about the possible seizure event including the label (such as, the start time, stop time, duration of a discrete seizure event or prevalence) and/or patient EEG data associated with the seizure event.

FIG. 16 illustrates a seizure detection output 1500, which can be presented as a graphical user interface on a display. Traces of EEG data obtained by individual EEG sensors (such as, four sensors 301 positioned at locations of the scalp approximate to F7, F8, TP9, and TP10 associated with the front left and right forehead positions and positions behind the left and right ear) as well as differential EEG data are presented in the chart or graph 1502. Differential EEG data can be obtained by combining EEG data obtained by the individual EEG sensors (for example, F8-TP10, F7-F8, TP9-TP10, F7-TP10, and F8-TP9). Illustrated traces of EEG data can be associated with a longitudinal transverse montage.

Detection of possible seizure events along with confidence levels are presented in the region 1504. For example, a possible seizure event 1510 is associated with a high confidence level. As another example, a possible seizure event 1512 is associated with a moderate confidence level. As described herein, the confidence level can assist a clinician with the determination of whether the detected seizure event is a true seizure. In some instances, the confidence value can be additionally or alternatively output.

As described herein (such as, with reference to FIGS. 4A and 4B), single or multiple seizure detection pathways can output seizure events. Events detected by multiple seizure detection pathways that overlap can be merged into a single seizure event. Outputs of the seizure detection pathways can be merged into a single seizure event. This can be performed, for instance, by the event merge block 460 of FIG. 4B. Suppose a first seizure event output by a first seizure detection pathway overlaps in time with a second seizure event output by a second seizure detection pathway. The first and second seizure events may be concatenated into a single seizure event for output. For instance, the first seizure event (which can be a discrete seizure event) can be associated with start time 10:00:00, stop time 10:00:35, and confidence level of 50%. The second seizure event can be associated with start time 10:00:20, stop time 10:00:48, and confidence level of 30%. A concatenated seizure event associated with start time 10:00:00, stop time 10:00:48, and confidence level of 30% may be output.

In some instances, one of the first or second seizure events can be retained while the other can be discarded. In some cases, a seizure event with the highest confidence can be retained. Continuing with the above example, the first seizure event can be retained and the second seizure event may be dropped. If both first and second seizure events are associated with the same confidence, an event of the shortest duration can be retained.

In some implementations, retention one of the seizure events can be performed based on the confidence values determined over time. For example, suppose that a seizure detection pathway A has been outputting high confidence seizure events over a duration of time, and a seizure detection pathway B has been outputting lower confidence seizure events over the duration of time. In case pathways A and B output seizure events with the same confidence at some later point in time, the seizure event provided by pathway A can be retained due to the pathway A outputting higher confidence seizure events in the past.

Additional Examples

The following provides example systems, methods, and computer-readable media for detecting discrete seizure events. The examples are not intended to limit the implementations described herein but are intended to illustrate the various implementations. Any of the features from a particular example can be combined with any other one or more features from any other one or more examples.

1. Differentiated Pathways

In some implementations, the techniques described herein relate to a method for detecting seizure events using electroencephalogram (EEG) signals, the method including: by first one or more processors: configuring a plurality of seizure detection pathways based on EEG data collected from a patient population with a first plurality of EEG sensors, each seizure detection pathway of the plurality of seizure detection pathways including one or more differentiated steps, and the plurality of seizure detection pathways being configured to detect differentiated electrographic seizure characteristics; and by second one or more processors: processing EEG data collected by a second plurality of EEG sensors from a patient being evaluated with the plurality of seizure detection pathways to provide a plurality of differentiated outputs relating to seizure events associated with the differentiated electrographic seizure characteristics; and outputting a label associated with a seizure event from the plurality of differentiated outputs relating to possible seizure events.

In some implementations, the techniques described herein relate to a method, wherein the label indicates a start time and duration of the seizure event.

In some implementations, the techniques described herein relate to a method, wherein the label indicates a prevalence of an electrographic seizure characteristic over a duration of time.

In some implementations, the techniques described herein relate to a method, wherein the plurality of seizure detection pathways includes a first seizure detection pathway configured to detect a first electrographic seizure characteristic indicative of an absence seizure, a second seizure detection pathway configured to detect a second electrographic seizure characteristic indicative of a tonic-clonic seizure, and a third seizure detection pathway configured to detect a third electrographic seizure characteristic indicative of a combination of two or more seizure types.

In some implementations, the techniques described herein relate to a method, wherein each seizure detection pathway of the plurality of seizure detection pathways includes: a preprocessing step, a segmenting step, a feature extraction step, a classification step, and an event identification step.

In some implementations, the techniques described herein relate to a method, wherein the plurality of seizure detection pathways are differentiated at the preprocessing step that includes standardizing the EEG data to account for inter-patient differences and within patient differences.

In some implementations, the techniques described herein relate to a method, wherein the plurality of seizure detection pathways are differentiated at the segmenting step.

In some implementations, the techniques described herein relate to a method, wherein the plurality of seizure detection pathways are differentiated at the feature extraction step that includes: identifying a plurality of features based on an electrographic seizure characteristic being detected by a seizure detection pathway; and extracting the plurality of features.

In some implementations, the techniques described herein relate to a method, wherein the plurality of seizure detection pathways are differentiated at the classification step that includes assigning a probability of occurrence of an electrographic seizure characteristic by applying a classifier tuned to detect the electrographic seizure characteristic.

In some implementations, the techniques described herein relate to a method, wherein the plurality of seizure detection pathways are differentiated at the event identification step that includes transforming one or more probabilities determined by the classifier to the label.

In some implementations, the techniques described herein relate to a method, further including, with second one or more processors: receiving one or more of patient physiological data acquired by one or more first sensors and environmental data acquired by one or more second sensors; and outputting the label further based on one or more of: the patient physiological data and the environmental data.

In some implementations, the techniques described herein relate to a non-transitory computer readable medium storing instructions that, when executed by first and second one or more processors, cause the first and second one or more processors to perform a method for detecting seizure events using electroencephalogram (EEG) signals, the method including: by first one or more processors: configuring a plurality of seizure detection pathways based on EEG data collected from a patient population with a first plurality of EEG sensors, each seizure detection pathway of the plurality of seizure detection pathways including one or more differentiated steps, and the plurality of seizure detection pathways being configured to detect differentiated electrographic seizure characteristics; and by second one or more processors: processing EEG data collected by a second plurality of EEG sensors from a patient being evaluated with the plurality of seizure detection pathways to provide a plurality of differentiated outputs relating to seizure events associated with the differentiated electrographic seizure characteristics; and outputting a label associated with a seizure event from the plurality of differentiated outputs relating to possible seizure events.

In some implementations, the techniques described herein relate to a non-transitory computer readable medium, wherein the label indicates a start time and duration of the seizure event.

In some implementations, the techniques described herein relate to a non-transitory computer readable medium, wherein the label indicates a prevalence of an electrographic seizure characteristic over a duration of time.

In some implementations, the techniques described herein relate to a non-transitory computer readable medium, wherein the plurality of seizure detection pathways includes a first seizure detection pathway configured to detect a first electrographic seizure characteristic indicative of an absence seizure, a second seizure detection pathway configured to detect a second electrographic seizure characteristic indicative of a tonic-clonic seizure, and a third seizure detection pathway configured to detect a third electrographic seizure characteristic indicative of a combination of two or more seizure types.

In some implementations, the techniques described herein relate to a non-transitory computer readable medium, wherein each seizure detection pathway of the plurality of seizure detection pathways includes: a preprocessing step, a segmenting step, a feature extraction step, a classification step, and an event identification step.

In some implementations, the techniques described herein relate to a non-transitory computer readable medium, wherein the plurality of seizure detection pathways are differentiated at the preprocessing step that includes standardizing the EEG data to account for inter-patient differences and within patient differences.

In some implementations, the techniques described herein relate to a non-transitory computer readable medium, wherein the plurality of seizure detection pathways are differentiated at the segmenting step.

In some implementations, the techniques described herein relate to a non-transitory computer readable medium, wherein the plurality of seizure detection pathways are differentiated at the feature extraction step that includes: identifying a plurality of features based on an electrographic seizure characteristic being detected by a seizure detection pathway; and extracting the plurality of features.

In some implementations, the techniques described herein relate to a non-transitory computer readable medium, wherein the plurality of seizure detection pathways are differentiated at the classification step that includes assigning a probability of occurrence of an electrographic seizure characteristic by applying a classifier tuned to detect the electrographic seizure characteristic.

In some implementations, the techniques described herein relate to a non-transitory computer readable medium, wherein the plurality of seizure detection pathways are differentiated at the event identification step that includes transforming one or more probabilities determined by the classifier to the label.

In some implementations, the techniques described herein relate to a non-transitory computer readable medium, further including, with second one or more processors: receiving one or more of patient physiological data acquired by one or more first sensors and environmental data acquired by one or more second sensors; and outputting the label further based on one or more of: the patient physiological data and the environmental data.

In some implementations, the techniques described herein relate to a system for detecting seizure events using electroencephalogram (EEG) signals including: a plurality of discrete wireless EEG sensors configured to be disposed on a scalp of a patient, each discrete wireless EEG sensor configured to collect an EEG data channel; and a non-transitory computer readable medium storing instructions thereon that, when executed by one or more processors, cause the one or more processors to perform the method of any of the preceding implementations.

2. Event Identification and Confidence

In some implementations, the techniques described herein relate to a method for detecting seizure events using electroencephalogram (EEG) signals, the method including: by first one or more processors: selecting from a plurality of event identifiers a set of event identifiers configured to transform a first plurality of probabilities of occurrence of one or more electrographic seizure characteristics in EEG data segments of training data into a first set of labels associated with a first seizure event, the first plurality of probabilities being determined by a classifier, and each event identifier of the set of event identifiers having a confidence value indicative of an accuracy with which the event identifier determines a label; and by second one or more processors: with the set of event identifiers, transforming a second plurality of probabilities of occurrence of the one or more electrographic seizure characteristics in EEG data segments collected from a patient into a second set of labels associated with a second seizure event, the second plurality of probabilities being determined by the classifier; outputting from the second set of labels a label determined by an event identifier with a highest confidence value of any other event identifier from the set of event identifiers; and providing a notification of the second seizure event along with a confidence level associated with the highest confidence value.

In some implementations, the techniques described herein relate to a method, wherein the second set of labels corresponds to start times and durations of discrete seizure events.

In some implementations, the techniques described herein relate to a method, wherein the second set of labels corresponds to a prevalence of an electrographic seizure characteristic over a duration of time, and wherein the outputted label further satisfies a prevalence threshold.

In some implementations, the techniques described herein relate to a method, wherein providing the notification of the second seizure event along with the confidence level associated with the highest confidence value includes displaying the notification along with the confidence level together with the EEG data segments collected from the patient.

In some implementations, the techniques described herein relate to a method, wherein the confidence level includes one of high, moderate, or low.

In some implementations, the techniques described herein relate to a method, wherein the EEG data segments are displayed as a longitudinal transverse montage that includes four channels of EEG data collected by four discrete wireless EEG sensors positioned at a left forehead, at a right forehead, behind a left ear, and behind a right ear of the patient and a plurality of channels derived by subtracting a pair of channels of the four channels of EEG data.

In some implementations, the techniques described herein relate to a method, wherein event identifiers of the set of event identifiers each have different parameterizations for transforming the second plurality of probabilities into a label of the second set of labels.

In some implementations, the techniques described herein relate to a method, wherein the highest confidence value corresponds to a highest precision.

In some implementations, the techniques described herein relate to a method, wherein outputting from the second set of labels the label determined by the event identifier with the highest confidence value of any other event identifier from the set of event identifiers includes discarding a label determined by another event identifier with a lower confidence than the event identifier.

In some implementations, the techniques described herein relate to a method, further including, by the second one or more processors: with another set of event identifiers, transforming another plurality of probabilities of occurrence of another one or more electrographic seizure characteristics in EEG data segments collected from the patient into another set of labels associated with another seizure event, the another plurality of probabilities being determined by another classifier; outputting from the another set of labels another label determined by an event identifier with a highest confidence value of any other event identifier from the another set of event identifiers; determining that a confidence value of the another label exceeds a confidence value of the label; and in response to determining that the confidence value of the another label exceeds the confidence value of the label, providing a notification of the another seizure event along with another confidence level associated with the another label.

In some implementations, the techniques described herein relate to a method, further including, by the second one or more processors: with another set of event identifiers, transforming another plurality of probabilities of occurrence of another one or more electrographic seizure characteristics in EEG data segments collected from the patient into another set of labels associated with another seizure event, the another plurality of probabilities being determined by another classifier; merging the second seizure event and the confidence level with the another seizure event and the another confidence level into a merged seizure event and a merged confidence level; and providing a notification of the merged seizure event along with the merged confidence level.

In some implementations, the techniques described herein relate to a non-transitory computer readable medium storing instructions that, when executed by first and second one or more processors, cause the first and second one or more processors to perform a method for detecting seizure events using electroencephalogram (EEG) signals, the method including: by first one or more processors: selecting from a plurality of event identifiers a set of event identifiers configured to transform a first plurality of probabilities of occurrence of one or more electrographic seizure characteristics in EEG data segments of training data into a first set of labels associated with a first seizure event, the first plurality of probabilities being determined by a classifier, and each event identifier of the set of event identifiers having a confidence value indicative of an accuracy with which the event identifier determines a label; and by second one or more processors: with the set of event identifiers, transforming a second plurality of probabilities of occurrence of the one or more electrographic seizure characteristics in EEG data segments collected from a patient into a second set of labels associated with a second seizure event, the second plurality of probabilities being determined by the classifier; outputting from the second set of labels a label determined by an event identifier with a highest confidence value of any other event identifier from the set of event identifiers; and providing a notification of the second seizure event along with a confidence level associated with the highest confidence value.

In some implementations, the techniques described herein relate to a non-transitory computer readable medium, wherein the second set of labels corresponds to start times and durations of discrete seizure events.

In some implementations, the techniques described herein relate to a non-transitory computer readable medium, wherein the second set of labels corresponds to a prevalence of an electrographic seizure characteristic over a duration of time, and wherein the outputted label further satisfies a prevalence threshold.

In some implementations, the techniques described herein relate to a non-transitory computer readable medium, wherein providing the notification of the second seizure event along with the confidence level associated with the highest confidence value includes displaying the notification along with the confidence level together with the EEG data segments collected from the patient.

In some implementations, the techniques described herein relate to a non-transitory computer readable medium, wherein the confidence level includes one of high, moderate, or low.

In some implementations, the techniques described herein relate to a non-transitory computer readable medium, wherein the EEG data segments are displayed as a longitudinal transverse montage that includes four channels of EEG data collected by four discrete wireless EEG sensors positioned at a left forehead, at a right forehead, behind a left ear, and behind a right ear of the patient and a plurality of channels derived by subtracting a pair of channels of the four channels of EEG data.

In some implementations, the techniques described herein relate to a non-transitory computer readable medium, wherein event identifiers of the set of event identifiers each have different parameterizations for transforming the second plurality of probabilities into a label of the second set of labels.

In some implementations, the techniques described herein relate to a non-transitory computer readable medium, wherein the highest confidence value corresponds to a highest precision.

In some implementations, the techniques described herein relate to a non-transitory computer readable medium, wherein outputting from the second set of labels the label determined by the event identifier with the highest confidence value of any other event identifier from the set of event identifiers includes discarding a label determined by another event identifier with a lower confidence than the event identifier.

In some implementations, the techniques described herein relate to a non-transitory computer readable medium, further including, by the second one or more processors: with another set of event identifiers, transforming another plurality of probabilities of occurrence of another one or more electrographic seizure characteristics in EEG data segments collected from the patient into another set of labels associated with another seizure event, the another plurality of probabilities being determined by another classifier; outputting from the another set of labels another label determined by an event identifier with a highest confidence value of any other event identifier from the another set of event identifiers; determining that a confidence value of the another label exceeds a confidence value of the label; and in response to determining that the confidence value of the another label exceeds the confidence value of the label, providing a notification of the another seizure event along with another confidence level associated with the another label.

In some implementations, the techniques described herein relate to a non-transitory computer readable medium, further including, by the second one or more processors: with another set of event identifiers, transforming another plurality of probabilities of occurrence of another one or more electrographic seizure characteristics in EEG data segments collected from the patient into another set of labels associated with another seizure event, the another plurality of probabilities being determined by another classifier; merging the second seizure event and the confidence level with the another seizure event and the another confidence level into a merged seizure event and a merged confidence level; and providing a notification of the merged seizure event along with the merged confidence level.

In some implementations, the techniques described herein relate to a system for detecting seizure events using electroencephalogram (EEG) signals including: a plurality of discrete wireless EEG sensors configured to be disposed on a scalp of a patient, each discrete wireless EEG sensor configured to collect an EEG data channel; and a non-transitory computer readable medium storing instructions thereon that, when executed by one or more processors, cause the one or more processors to perform the method of any of the preceding implementations.

3. Adaptive Preprocessing

In some implementations, the techniques described herein relate to a method of detecting seizure events from electroencephalogram (EEG) signals including: with one or more processors: preprocessing patient EEG data collected, from a scalp of a particular patient, by a plurality of discrete wireless EEG sensors to obtain preprocessed patient EEG data, wherein at least one parameter of the preprocessing changes over time responsive to a change in the patient EEG data; and detecting a seizure event from the preprocessed patient EEG data.

In some implementations, the techniques described herein relate to a method, wherein the patient EEG data is independently collected by each discrete wireless EEG sensor of the plurality of discrete wireless EEG sensors.

In some implementations, the techniques described herein relate to a method, wherein preprocessing includes standardizing the patient EEG data by: determining variances of the patient EEG data of a plurality of segments of the patient EEG data; and modifying one or more segments of the patient EEG data with variances that do not satisfy a variance threshold that changes based on the variances of the plurality of segments.

In some implementations, the techniques described herein relate to a method, wherein responsive to a current value of the variance threshold being larger than a variance of a segment of the patient EEG data, setting the variance threshold to the variance of the segment of the patient EEG data.

In some implementations, the techniques described herein relate to a method, wherein the variance threshold is increased by a multiplier responsive to not encountering a segment of the patient EEG data with a variance that is smaller than the current value of the variance threshold during a threshold period of time.

In some implementations, the techniques described herein relate to a method, further including monitoring the patient EEG data for the change in the patient EEG data and adjusting the at least one parameter of the preprocessing responsive to the change in the patient EEG data.

In some implementations, the techniques described herein relate to a method, wherein the change is due to a position or orientation of a discrete wireless EEG sensor of the plurality of discrete wireless EEG sensors.

In some implementations, the techniques described herein relate to a method, wherein adjusting the at least one parameter of the preprocessing is performed responsive to not detecting a change in the patient EEG data over a duration of time.

In some implementations, the techniques described herein relate to a method, wherein the plurality of discrete wireless EEG sensors are configured to collect the patient EEG data without a common reference electrode.

In some implementations, the techniques described herein relate to a method, wherein preprocessing further includes denoising the patient EEG data to remove at least one frequency component in the patient EEG data.

In some implementations, the techniques described herein relate to a method, wherein denoising includes: identifying one or more noise signals in the patient EEG data; and removing the one or more noise signals from the patient EEG data.

In some implementations, the techniques described herein relate to a method, wherein identifying the one or more noise signals includes: dividing the patient EEG data into a plurality of segments; and identifying the one or more noise signals responsive to a determination that linear combinations of frequency components do not satisfy a threshold associated with a frequency variance.

In some implementations, the techniques described herein relate to a non-transitory computer readable medium storing instructions that, when executed by one or more processors, cause the one or more processors to: preprocess patient EEG data collected, from a scalp of a particular patient, by a plurality of discrete wireless EEG sensors to obtain preprocessed patient EEG data, wherein at least one parameter of the preprocessing changes over time responsive to a change in the patient EEG data; and detect a seizure event from the preprocessed patient EEG data.

In some implementations, the techniques described herein relate to a non-transitory computer readable medium, wherein the patient EEG data is independently collected by each discrete wireless EEG sensor of the plurality of discrete wireless EEG sensors.

In some implementations, the techniques described herein relate to a non-transitory computer readable medium, wherein preprocessing includes standardizing the patient EEG data by: determining variances of the patient EEG data of a plurality of segments of the patient EEG data; and modifying one or more segments of the patient EEG data with variances that do not satisfy a variance threshold that changes based on the variances of the plurality of segments.

In some implementations, the techniques described herein relate to a non-transitory computer readable medium, wherein the instructions are further configured to cause the one or more processors to, responsive to a current value of the variance threshold being larger than the variance of a segment of the patient EEG data, setting the variance threshold to the variance of the segment of the patient EEG data.

In some implementations, the techniques described herein relate to a non-transitory computer readable medium, wherein the variance threshold is increased by a multiplier responsive to not encountering a segment of the patient EEG data with a variance that is smaller than the current value of the variance threshold during a threshold period of time.

In some implementations, the techniques described herein relate to a non-transitory computer readable medium, wherein the instructions are further configured to cause the one or more processors to monitor the patient EEG for the change in the EEG data and adjust the at least one parameter of the preprocessing responsive to the change in the EEG data.

In some implementations, the techniques described herein relate to a non-transitory computer readable medium, wherein the change is due to a position or orientation of a discrete wireless EEG sensor of the plurality of discrete wireless EEG sensors.

In some implementations, the techniques described herein relate to a non-transitory computer readable medium, wherein adjusting the at least one parameter of the preprocessing is performed responsive to not detecting a change in the patient EEG data over a duration of time.

In some implementations, the techniques described herein relate to a non-transitory computer readable medium, wherein the plurality of discrete wireless EEG sensors are configured to collect the patient EEG data without a common reference electrode.

In some implementations, the techniques described herein relate to a non-transitory computer readable medium, wherein the instructions are further configured to cause the one or more processors to preprocess the patient EEG data by denoising the patient EEG data to remove at least one frequency component in the patient EEG data.

In some implementations, the techniques described herein relate to a non-transitory computer readable medium, wherein the instructions are further configured to cause the one or more processors to denoise the patient EEG data by: identifying one or more noise signals in the patient EEG data; and removing the one or more noise signals from the patient EEG data.

In some implementations, the techniques described herein relate to a non-transitory computer readable medium, wherein the instructions are further configured to cause the one or more processors to identify the one or more noise signals by: dividing the patient EEG data into a plurality of segments; and identifying the one or more noise signals responsive to a determination that linear combinations of frequency components do not satisfy a threshold associated with a frequency variance.

In some implementations, the techniques described herein relate to a system for detecting seizure events from electroencephalogram (EEG) signals including: a plurality of EEG sensors configured to be placed on a scalp of a particular patient and collect patient EEG data; and a non-transitory computer readable memory storing instructions thereon that, when executed by one or more processors, cause the one or more processors to: preprocess patient EEG data collected, from a scalp of a particular patient, by a plurality of discrete wireless EEG sensors to obtain preprocessed patient EEG data, wherein at least one parameter of the preprocessing changes over time responsive to a change in the patient EEG data; and detect a seizure event from the preprocessed patient EEG data.

In some implementations, the techniques described herein relate to a system, wherein the patient EEG data is independently collected by each discrete wireless EEG sensor of the plurality of discrete wireless EEG sensors.

In some implementations, the techniques described herein relate to a system, wherein the instructions are further configured to cause the one or more processors to standardize the patient EEG data by: determining variances of the patient EEG data of a plurality of segments of the patient EEG data; and modifying one or more segments of the patient EEG data with variances that do not satisfy a variance threshold that changes based on the variances of the plurality of segments.

In some implementations, the techniques described herein relate to a system, wherein the instructions are further configured to cause the one or more processors to, responsive to a current value of the variance threshold being larger than the variance of a segment of the patient EEG data, setting the variance threshold to the variance of the segment of the patient EEG data.

In some implementations, the techniques described herein relate to a system, wherein the variance threshold is increased by a multiplier responsive to not encountering a segment of the patient EEG data with a variance that is smaller than the current value of the variance threshold during a threshold period of time.

In some implementations, the techniques described herein relate to a system, wherein the instructions are further configured to cause the one or more processors to monitor the patient EEG for the change in the EEG data and adjust the at least one parameter of the preprocessing responsive to the change in the EEG data.

In some implementations, the techniques described herein relate to a system, wherein the change is due to a position or orientation of a discrete wireless EEG sensor of the plurality of discrete wireless EEG sensors.

In some implementations, the techniques described herein relate to a system, wherein adjusting the at least one parameter of the preprocessing is performed responsive to not detecting a change in the EEG data over a duration of time.

In some implementations, the techniques described herein relate to a system, wherein the plurality of discrete wireless EEG sensors are further configured to collect the patient EEG data without a common reference electrode.

In some implementations, the techniques described herein relate to a system, wherein the instructions are further configured to cause the one or more processors to preprocess the patient EEG data by denoising the patient EEG data to remove at least one frequency component in the patient EEG data.

In some implementations, the techniques described herein relate to a system, wherein the instructions are further configured to cause the one or more processors to denoise the patient EEG data by: identifying one or more noise signals in the patient EEG data; and removing the one or more noise signals from the patient EEG data.

In some implementations, the techniques described herein relate to a system, wherein the instructions are further configured to cause the one or more processors to identify the one or more noise signals by: dividing the patient EEG data into a plurality of segments; and identifying the one or more noise signals responsive to a determination that linear combinations of frequency components do not satisfy a threshold associated with a frequency variance.

4. Augmentation of EEG Data Features (Meta-Features) and Channel Augmentation (Synthetic EEG Data Channel)

In some implementations, the techniques described herein relate to a method for detecting seizure events from electroencephalogram (EEG) signals including: segmenting data collected from a plurality of EEG data channels, each EEG data channel being collected by a discrete wireless EEG sensor of a plurality of discrete wireless EEG sensors disposed on a scalp of a patient, the segmenting forming a plurality of EEG data segments; extracting a plurality of features from the plurality of EEG data segments to form an extracted feature dataset associated with each EEG data channel of the plurality of EEG data channels from which the data was collected; creating a meta-feature from at least one feature from the plurality of features; and detecting a seizure event based at least on the meta-feature, wherein the method is performed by one or more processors.

In some implementations, the techniques described herein relate to a method, wherein creating the meta-feature includes pooling values for the at least one feature.

In some implementations, the techniques described herein relate to a method, wherein the plurality of EEG data channels includes four EEG data channels collected by four discrete wireless EEG sensors disposed at a left forehead, at a right forehead, behind a left ear, and behind a right ear of the patient.

In some implementations, the techniques described herein relate to a method, wherein: detecting the seizure event includes using a classifier; and the meta-feature is used to train the classifier.

In some implementations, the techniques described herein relate to a method, wherein: each discrete wireless EEG sensor of the plurality of discrete wireless EEG sensors collects an EEG data channel independently from the other discrete wireless EEG sensors of the plurality of discrete wireless EEG sensors; and creating the meta-feature includes generalizing EEG data across two or more EEG data channels of the plurality of EEG data channels thereby pooling EEG data of the two or more EEG data channels together for detection of the seizure event.

In some implementations, the techniques described herein relate to a method, wherein detecting the seizure event is further based on one or more features from the plurality of features.

In some implementations, the techniques described herein relate to a method, wherein the meta-feature removes a bias in the plurality of EEG data channels toward a particular location on the scalp for detection of the seizure event.

In some implementations, the techniques described herein relate to an electroencephalogram (EEG) system including: a plurality of discrete wireless EEG sensors configured to be disposed on a scalp of a patient, each discrete wireless EEG sensor configured to collect an EEG data channel of a plurality of EEG data channels; and a non-transitory computer readable medium with instructions stored thereon that, when executed by one or more processors, cause the one or more processors to: form a plurality of EEG data segments by segmenting the plurality of EEG data channels; extract a plurality of features from the plurality of EEG data segments to form an extracted feature dataset associated with each EEG data channel of the plurality of EEG data channels from which the data was collected; create a meta-feature from at least one feature from the plurality of features; and detect a seizure event based at least on the meta-feature.

In some implementations, the techniques described herein relate to a system, the meta-feature is created by pooling values for the at least one feature.

In some implementations, the techniques described herein relate to a system, wherein the plurality of discrete wireless EEG sensors includes four discrete wireless EEG sensors configured to be disposed at a left forehead, at a right forehead, behind a left ear, and behind a right ear of the patient.

In some implementations, the techniques described herein relate to a system, where wherein the instructions are further configured to cause the one or more processors to detect the seizure event by using a classifier, wherein the meta-feature is used to train the classifier.

In some implementations, the techniques described herein relate to a system, wherein: each discrete wireless EEG sensor of the plurality of discrete wireless EEG sensors collects an EEG data channel independently from the other discrete wireless EEG sensors of the plurality of discrete wireless EEG sensors; and creating the meta-feature includes generalizing EEG data across two or more EEG data channels of the plurality of EEG data channels thereby pooling EEG data of the two or more EEG data channels together for detection of the seizure event.

In some implementations, the techniques described herein relate to a system, wherein the seizure event is detected further based on one or more features from the plurality of features.

In some implementations, the techniques described herein relate to a system, wherein the meta-feature removes a bias in the plurality of EEG data channels toward a particular location on the scalp for detection of the seizure event.

In some implementations, the techniques described herein relate to a method for detecting seizure events in a patient including: by first one or more processors, receiving EEG data from a plurality of discrete wireless EEG sensors, each discrete wireless EEG sensor providing an EEG data channel of a plurality of EEG data channels; generating at least one synthetic EEG data channel based on the plurality of EEG data channels; and training a seizure detection model based on the at least one synthetic EEG data channel and the plurality of EEG data channels; and by second one or more processors, detecting a seizure event by applying the seizure detection model to at least four data channels provided by at least four discrete wireless EEG sensors positioned on a scalp of a particular patient.

In some implementations, the techniques described herein relate to a method, wherein the at least one synthetic EEG data channel is created by augmenting at least one EEG data channel of the plurality of EEG data channels.

In some implementations, the techniques described herein relate to a method, wherein augmenting includes scaling at least one EEG data channel.

In some implementations, the techniques described herein relate to a method, wherein scaling the at least one EEG data channel includes flipping the at least one EEG data channel.

In some implementations, the techniques described herein relate to a method, wherein augmenting includes adding noise to at least one EEG data channel.

In some implementations, the techniques described herein relate to an electroencephalogram (EEG) system including: a plurality of discrete wireless EEG sensors configured to be disposed on a scalp of a patient, each discrete wireless EEG sensor configured to collect an EEG data channel; and a non-transitory computer readable medium with instructions stored thereon that, when executed by first and second one or more processors, cause the first one or more processors to: receive EEG data from a plurality of discrete wireless EEG sensors, each discrete wireless EEG sensor providing an EEG data channel; generate at least one synthetic EEG data channel based on the plurality of EEG data channels; and train a seizure detection model based on the at least one synthetic EEG data channel and the plurality of EEG data channels; and cause the second one or more processors to: detect a seizure event by applying the seizure detection model to at least four data channels provided by at least four discrete wireless EEG sensors positioned on a scalp of a particular patient.

In some implementations, the techniques described herein relate to a system, wherein the at least one synthetic EEG data channel is created by augmenting at least one EEG data channel of the plurality of EEG data channels.

In some implementations, the techniques described herein relate to a system, wherein augmenting includes scaling at least one EEG data channel.

In some implementations, the techniques described herein relate to a system, wherein scaling the at least one EEG data channel includes flipping the at least one EEG data channel.

In some implementations, the techniques described herein relate to a system, wherein augmenting includes adding noise to at least one EEG data channel.

In some implementations, the techniques described herein relate to a non-transitory computer-readable medium storing instructions that, when executed by one or more processors, cause the one or more processors to implement the method of any of the preceding implementations.

5. Identifying Seizure Events

In some implementations, the techniques described herein relate to a method of detecting seizure events from electroencephalogram (EEG) signals including: segmenting EEG data collected by a plurality of discrete wireless EEG sensors disposed on a scalp a particular patient to form a plurality of segments; determining probabilities of occurrence of one or more electrographic seizure characteristics for the plurality of segments; modifying a probability of a segment of the plurality of segments using one or more probabilities of one or more adjacent segments of the plurality of segments; and detecting a discrete seizure event spanning the segment of the plurality of segments and the one or more adjacent segments of the plurality of segments, wherein the method is performed by one or more processors.

In some implementations, the techniques described herein relate to a method, modifying the probability of the segment includes performing at least one morphological transformation that uses the probability of the segment and the one or more probabilities of the one or more adjacent segments.

In some implementations, the techniques described herein relate to a method, wherein the at least one morphological transformation includes a morphological closure.

In some implementations, the techniques described herein relate to a method, further including performing an exponential moving average of the probabilities of the plurality of segments prior to modifying the probability of the segment.

In some implementations, the techniques described herein relate to a method, wherein detecting the discrete seizure event is performed with a sensitivity of at least 80% and a false positive rate of no more than 0.08 per hour.

In some implementations, the techniques described herein relate to a method, wherein the discrete seizure event has a duration between 10 seconds and 15 minutes.

In some implementations, the techniques described herein relate to a method, further including discarding the discrete seizure event in response to determining that the duration of the discrete seizure event exceeds 15 minutes.

In some implementations, the techniques described herein relate to a method, further including: in response to detecting a first discrete seizure event and a second discrete seizure event that begins within a threshold time duration of an end of the first discrete seizure event, combining the first and second discrete seizure events into a single discrete seizure event.

In some implementations, the techniques described herein relate to a method, wherein the threshold time duration includes 2 minutes.

In some implementations, the techniques described herein relate to an electroencephalogram (EEG) system including: a plurality of discrete wireless EEG sensors configured to be disposed on a scalp of a patient, each discrete wireless EEG sensor configured to collect an EEG data channel; and a non-transitory computer-readable medium storing instructions that, when executed by one or more processors, cause the one or more processors to: segment EEG data collected by a plurality of discrete wireless EEG sensors disposed on a scalp a particular patient to form a plurality of segments; determine probabilities of occurrence of one or more electrographic seizure characteristics for the plurality of segments; modify a probability of a segment of the plurality of segments using one or more probabilities of one or more adjacent segments of the plurality of segments; and detect a discrete seizure event spanning the segment of the plurality of segments and the one or more adjacent segments of the plurality of segments.

In some implementations, the techniques described herein relate to a system, wherein the instructions are further configured to cause the one or more processors to modify the probability of the segment by performing at least one morphological transformation that uses the probability of the segment and the one or more probabilities of the one or more adjacent segments.

In some implementations, the techniques described herein relate to a system, wherein the at least one morphological transformation includes a morphological closure.

In some implementations, the techniques described herein relate to a system, wherein the instructions are further configured to cause the one or more processors to detect the discrete seizure event with a sensitivity of at least 80% and a false positive rate of no more than 0.08 per hour.

In some implementations, the techniques described herein relate to a system, wherein the discrete seizure event has a duration between 10 seconds and 15 minutes.

In some implementations, the techniques described herein relate to a system, wherein the instructions are further configured to cause the one or more processors to discard the discrete seizure event in response to determining that the duration of the discrete seizure event exceeds 15 minutes.

In some implementations, the techniques described herein relate to a system, wherein the instructions are further configured to cause the one or more processors to: in response to detecting a first discrete seizure event and a second discrete seizure event that begins within a threshold time duration of an end of the first discrete seizure event, combining the first and second discrete seizure events into a single discrete seizure event.

In some implementations, the techniques described herein relate to the system of implementation 16, wherein the threshold time duration includes 2 minutes.

In some implementations, the techniques described herein relate to a non-transitory computer-readable medium storing instructions that, when executed by one or more processors, cause the one or more processors to implement the method of any of the preceding implementations.

6. Channel Augmentation

In some implementations, the techniques described herein relate to a method for detecting seizure events in a patient including: processing EEG data collected by a plurality of discrete wireless EEG sensors disposed on a scalp of a particular patient, each discrete wireless EEG sensor providing an EEG data channel; detecting a missing EEG data channel in the EEG data; creating a model EEG data channel using one or more EEG data channels present in the EEG data; and detecting a seizure event based on the one or more EEG data channels present in the EEG data and the model EEG data channel, wherein the method is performed by one or more processors.

In some implementations, the techniques described herein relate to a method, wherein the plurality of discrete wireless EEG sensors includes four discrete wireless sensors.

In some implementations, the techniques described herein relate to a method, wherein the model EEG data channel is created based on a stochastic sampling and emulation of the one or more EEG data channels present in the EEG data.

In some implementations, the techniques described herein relate to a method, wherein the model EEG data channel is created using shadow manifold cross sampling of the one or more EEG data channels present in the EEG data.

In some implementations, the techniques described herein relate to a method, wherein the model EEG data channel is created further based on EEG data collected from a patient population.

In some implementations, the techniques described herein relate to a method, wherein the model EEG data channel is created based on at least one EEG data channel collected by at least one discrete wireless EEG sensor of the plurality of discrete wireless EEG sensors that spatially corresponds with a discrete wireless EEG sensor associated with the missing EEG data channel.

In some implementations, the techniques described herein relate to a method, wherein the at least one discrete wireless EEG sensor is disposed on an opposite side of a medial plane than the discrete wireless EEG sensor associated with the missing EEG data channel.

In some implementations, the techniques described herein relate to a method, wherein the at least one discrete wireless EEG sensor is disposed on an opposite side of a frontal plane than the discrete wireless EEG sensor associated with the missing EEG data channel.

In some implementations, the techniques described herein relate to a method, wherein the missing EEG data channel in the EEG data is detected as a result of a failure of a discrete wireless EEG sensor of the plurality of discrete wireless EEG sensors.

In some implementations, the techniques described herein relate to an electroencephalogram (EEG) system including: a plurality of discrete wireless EEG sensors configured to be disposed on a scalp of a patient, each discrete wireless EEG sensor configured to collect an EEG data channel; and a non-transitory computer-readable medium storing instructions that, when executed by one or more processors, cause the one or more processors to: process EEG data collected by a plurality of discrete wireless EEG sensors disposed on a scalp of a particular patient, each discrete wireless EEG sensor providing an EEG data channel; detect a missing EEG data channel in the EEG data; create a model EEG data channel using one or more EEG data channels present in the EEG data; and detect a seizure event based on the one or more EEG data channels present in the EEG data and the model EEG data channel.

In some implementations, the techniques described herein relate to a system, wherein the plurality of discrete wireless EEG sensors includes four discrete wireless sensors.

In some implementations, the techniques described herein relate to a system, wherein the model EEG data channel is created based on a stochastic sampling and emulation of the one or more EEG data channels present in the EEG data.

In some implementations, the techniques described herein relate to a system, wherein the model EEG data channel is created using shadow manifold cross sampling of the one or more EEG data channels present in the EEG data.

In some implementations, the techniques described herein relate to a system, wherein the model EEG data channel is created further based on EEG data collected from a patient population.

In some implementations, the techniques described herein relate to a system, wherein the model EEG data channel is created based on at least one EEG data channel collected by at least one discrete wireless EEG sensor of the plurality of discrete wireless EEG sensors that spatially corresponds with a discrete wireless EEG sensor associated with the missing EEG data channel.

In some implementations, the techniques described herein relate to a system, wherein the at least one discrete wireless EEG sensor is disposed on an opposite side of a medial plane than the discrete wireless EEG sensor associated with the missing EEG data channel.

In some implementations, the techniques described herein relate to a system, wherein the at least one discrete wireless EEG sensor is disposed on an opposite side of a frontal plane than the discrete wireless EEG sensor associated with the missing EEG data channel.

In some implementations, the techniques described herein relate to a system, wherein the missing EEG data channel in the EEG data is detected as a result of a failure of a discrete wireless EEG sensor of the plurality of discrete wireless EEG sensors.

In some implementations, the techniques described herein relate to a non-transitory computer-readable medium storing instructions that, when executed by one or more processors, cause the one or more processors to implement the method of any of the preceding implementations.

Other Variations

Additional details of EEG monitoring systems and methods are described in U.S. Pat. No. 11,020,035, U.S. Patent Publication No. 2021/0307672, and U.S. patent application Ser. No. 18/067,611, filed on Dec. 16, 2022, each of which is incorporated by reference in its entirety.

The general principles described herein may be extended to other scenarios. For example, for intensive care in pediatric and adults two sensors, four sensors, eight sensors, or various combination of sensors may be used.

Various other configurations are may also be used, with particular elements that are depicted as being implemented in hardware may instead be implemented in software, firmware, or a combination thereof. One of ordinary skill in the art will recognize various alternatives to the specific embodiments described herein.

The specification and figures describe particular embodiments which are provided for ease of description and illustration and are not intended to be restrictive. Embodiments may be implemented to be used in various environments without departing from the spirit and scope of the disclosure.

At least some elements of implementations of one or more disclosed devices of the can be controlled and at least some steps of implementations of one or more disclosed methods can be effectuated, in operation with a programmable processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the disclosed implementations may be delivered to a processor in many forms, including, but not limited to, information permanently stored on non-writable storage media (for example read-only memory devices within a computer, such as ROM, or devices readable by a computer I/O attachment, such as CD-ROM or DVD disks), information alterably stored on writable storage media (for example floppy disks, removable flash memory and hard drives) or information conveyed to a computer through communication media, including wired or wireless computer networks. In addition, while some implementations may be embodied in software, the functions necessary to implement the disclosed features may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

In various embodiments, input from a user may be requested. Examples of methods for receiving user input, such as receiving a button press from a user, are illustrative and not by means of limitation. Alternative methods of receiving user input may be used, including receiving a button press on a touch screen, a physical button press on a device, a swipe, a tap, any other touch gestures, a spoken (audio) input, etc.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Depending on the embodiment, certain acts, events, or functions of any of the processes or algorithms described herein can be performed in a different sequence, can be added, merged, or left out altogether. Moreover, in certain embodiments, operations or events can be performed concurrently, for example, through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a machine learning service server, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A machine learning service server can be or include a microprocessor, but in the alternative, the machine learning service server can be or include a controller, microcontroller, or state machine, combinations of the same, or the like configured to generate and publish machine learning services backed by a machine learning model. A machine learning service server can include electrical circuitry configured to process computer-executable instructions. Although described herein primarily with respect to digital technology, a machine learning service server may also include primarily analog components. For example, some or all of the modeling, simulation, or service algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a machine learning service server, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An illustrative storage medium can be coupled to the machine learning service server such that the machine learning service server can read information from, and write information to, the storage medium. In the alternative, the storage medium can be integral to the machine learning service server. The machine learning service server and the storage medium can reside in an ASIC. The ASIC can reside in a user terminal. In the alternative, the machine learning service server and the storage medium can reside as discrete components in a user terminal (for example, access device or network service client device).

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A method for detecting seizure events using electroencephalogram (EEG) signals, the method comprising, by one or more processors:
   obtaining one or more EEG data segments collected by a plurality of EEG sensors positioned on a scalp of a patient;
   processing each of the one or more EEG data segments to obtain a plurality of probabilities of occurrence of one or more electrographic seizure characteristics;
   interpreting, by each of a plurality of event identifiers, the plurality of probabilities to obtain a plurality of event interpretations, each event interpretation reflecting a confidence value that represents a confidence of the interpretation being a true positive event;
   selecting an event interpretation from the plurality of event interpretations based on the confidence values; and
   outputting a label indicating 1) a seizure event based on the selected event interpretation and 2) a confidence indicator determined based on the confidence value of the selected event interpretation, the confidence indicator reflecting a confidence in the seizure event being a true positive event.

2. The method of claim 1, wherein the label indicates a start time and duration of a discrete seizure event.

3. The method of claim 1, wherein the label indicates a prevalence of an electrographic seizure characteristic over a duration of time.

4. The method of claim 1, wherein outputting the label comprises displaying the seizure event along with the confidence indicator together with the one or more EEG data segments.

5. The method of claim 4, wherein the one or more EEG data segments are displayed as a longitudinal transverse montage that comprises four channels of EEG data collected by four discrete wireless EEG sensors positioned at a left forehead, at a right forehead, behind a left ear, and behind a right ear of the patient and a plurality of channels derived from at least two channels of the four channels of EEG data.

6. The method of claim 1, wherein the confidence indicator comprises one of a plurality of confidence value ranges associated with high, moderate, and/or low confidence.

7. The method of claim 1, wherein selecting the event interpretation from the plurality of event interpretations comprises selecting an event interpretation reflecting the highest confidence value.

8. The method of claim 1, further comprising:
   merging the seizure event with another seizure event into a merged seizure event, wherein outputting the label comprises outputting a merged label indicating 1) the merged seizure event and 2) a merged confidence indicator that reflects a confidence in the merged seizure event being a true positive event.

9. The method of claim 1, wherein each event identifier combines temporal sequences of the plurality of probabilities to output a presence or absence of the seizure event.

10. The method of claim 1, wherein the processing comprises processing by one or more classifiers each of the one or more EEG data segments to obtain the plurality of probabilities.

11. A non-transitory computer readable medium storing instructions that, when executed by one or more processors, cause the one or more processors to perform a method for detecting seizure events using electroencephalogram (EEG) signals, the method comprising:
- obtaining one or more EEG data segments collected by a plurality of EEG sensors positioned on a scalp of a patient;
- processing each of the one or more EEG data segments to obtain a plurality of probabilities of occurrence of one or more electrographic seizure characteristics;
- interpreting, by each of a plurality of event identifiers, the plurality of probabilities to obtain a plurality of event interpretations, each event interpretation reflecting a confidence value that represents a confidence of the interpretation being a true positive event;
- selecting an event interpretation from the plurality of event interpretations based on the confidence values; and
- outputting a label indicating 1) a seizure event based on the selected event interpretation and 2) a confidence indicator determined based on the confidence value of the selected event interpretation, the confidence indicator reflecting a confidence in the seizure event being a true positive event.

12. The non-transitory computer readable medium of claim 11, wherein the label indicates a start time and duration of a discrete seizure event.

13. The non-transitory computer readable medium of claim 11, wherein the label indicates a prevalence of an electrographic seizure characteristic over a duration of time.

14. The non-transitory computer readable medium of claim 11, wherein outputting the label comprises displaying the seizure event along with the confidence indicator together with the one or more EEG data segments.

15. The non-transitory computer readable medium of claim 14, wherein the one or more EEG data segments are displayed as a longitudinal transverse montage that comprises four channels of EEG data collected by four discrete wireless EEG sensors positioned at a left forehead, at a right forehead, behind a left ear, and behind a right ear of the patient and a plurality of channels derived from at least two channels of the four channels of EEG data.

16. The non-transitory computer readable medium of claim 11, wherein the confidence indicator comprises one of a plurality of confidence value ranges associated with high, moderate, and/or low confidence.

17. The non-transitory computer readable medium of claim 11, wherein selecting the event interpretation from the plurality of event interpretations comprises selecting an event interpretation reflecting the highest confidence.

18. The non-transitory computer readable medium of claim 11, wherein the method further comprises:
- merging the seizure event with another seizure event into a merged seizure event, wherein outputting the label comprises outputting a merged label indicating 1) the merged seizure event and 2) a merged confidence indicator that reflects a confidence in the merged seizure event being a true positive event.

19. The non-transitory computer readable medium of claim 11, wherein each event identifier is configured to combine temporal sequences of the plurality of probabilities to output a presence or absence of the seizure event.

20. The non-transitory computer readable medium of claim 11, wherein the processing comprises processing by one or more classifiers each of the one or more EEG data segments to obtain the plurality of probabilities.

* * * * *